(12) United States Patent
Shabaz

(10) Patent No.: US 11,793,497 B2
(45) Date of Patent: *Oct. 24, 2023

(54) CORE NEEDLE BIOPSY DEVICE

(71) Applicant: C. R. Bard, Inc., Franklin Lakes, NJ (US)

(72) Inventor: Martin Victor Shabaz, Lake Forest, CA (US)

(73) Assignee: C.R. Bard, Inc., Murray Hill, NJ (US)

( * ) Notice: Subject to any disclaimer, the term of this patent is extended or adjusted under 35 U.S.C. 154(b) by 269 days.

This patent is subject to a terminal disclaimer.

(21) Appl. No.: 17/235,519

(22) Filed: Apr. 20, 2021

(65) Prior Publication Data

US 2021/0236098 A1 Aug. 5, 2021

Related U.S. Application Data

(63) Continuation of application No. 15/895,116, filed on Feb. 13, 2018, now Pat. No. 11,013,499, which is a
(Continued)

(51) Int. Cl.
*A61B 5/00* (2006.01)
*A61B 10/02* (2006.01)

(52) U.S. Cl.
CPC ...... *A61B 10/0266* (2013.01); *A61B 10/0275* (2013.01); *A61B 2010/0208* (2013.01)

(58) Field of Classification Search
CPC ............ A61B 10/0266; A61B 10/0275; A61B 2010/0208
See application file for complete search history.

(56) References Cited

U.S. PATENT DOCUMENTS 3,561,429 A 2/1971 Jewett
4,177,814 A 12/1979 Knepshield et al.
(Continued)

FOREIGN PATENT DOCUMENTS

DE 102008038413 A1 2/2010
EP 2785255 A1 10/2014
(Continued)

OTHER PUBLICATIONS

International Search Report / Written Opinion of the International Searching Authority for PCT/US2013/070975 dated Apr. 17, 2014.

*Primary Examiner* — May A Abouelela
(74) *Attorney, Agent, or Firm* — Dinsmore & Shohl LLP

(57) ABSTRACT

A biopsy device includes a cutting cannula mechanism having a cutting cannula and an inner stylet mechanism having an inner stylet coaxial with the cutting cannula. A cocking mechanism is configured to cock the cutting cannula mechanism and the inner stylet mechanism by retracting each of the cutting cannula and the inner stylet in a proximal direction to a cocked position. A trigger device is configured to fire at least one of the inner stylet mechanism and the cutting cannula mechanism to advance a respective at least one of the inner stylet and the cutting cannula from the cocked position in a distal direction. A selector assembly includes a selector switch having an exterior tab accessible by a user. The selector assembly is configured to select between at least two user selectable operating modes and at least two user selectable firing distances.

20 Claims, 19 Drawing Sheets

Related U.S. Application Data continuation of application No. 14/432,650, filed as application No. PCT/US2013/070975 on Nov. 20, 2013, now Pat. No. 9,968,338.

(60) Provisional application No. 61/774,293, filed on Mar. 7, 2013, provisional application No. 61/729,245, filed on Nov. 21, 2012.

(56) References Cited

U.S. PATENT DOCUMENTS

| | | |
|---|---|---|
| 4,230,123 A | 10/1980 | Hawkins, Jr. |
| 4,401,124 A | 8/1983 | Guess et al. |
| 4,600,014 A | 7/1986 | Beraha |
| 4,667,684 A | 5/1987 | Leigh |
| 4,699,154 A | 10/1987 | Lindgren |
| D295,315 S | 4/1988 | Nelson |
| 4,735,215 A | 4/1988 | Goto et al. |
| 4,763,667 A | 8/1988 | Manzo |
| 4,793,363 A | 12/1988 | Ausherman et al. |
| 4,869,259 A | 9/1989 | Elkins |
| 4,881,551 A | 11/1989 | Taylor |
| 4,907,599 A * | 3/1990 | Taylor ............ A61B 10/0275 606/1 |
| 4,924,878 A | 5/1990 | Nottke |
| 4,940,061 A | 7/1990 | Terwilliger et al. |
| 4,944,308 A | 7/1990 | Akerfeldt |
| 4,950,265 A | 8/1990 | Taylor |
| 4,953,558 A | 9/1990 | Akerfeldt |
| 4,958,625 A | 9/1990 | Bates et al. |
| 4,976,269 A | 12/1990 | Mehl |
| 4,977,897 A | 12/1990 | Hurwitz |
| D315,407 S | 3/1991 | Bradrick et al. |
| 5,025,797 A | 6/1991 | Baran |
| 5,036,860 A * | 8/1991 | Leigh ............ A61B 10/0275 606/171 |
| 5,048,530 A | 9/1991 | Hurwitz |
| 5,048,538 A | 9/1991 | Terwilliger et al. |
| 5,081,997 A | 1/1992 | Bosley, Jr. et al. |
| 5,090,419 A | 2/1992 | Palestrant |
| 5,146,921 A | 9/1992 | Terwilliger et al. |
| 5,156,160 A | 10/1992 | Bennett |
| 5,161,542 A | 11/1992 | Palestrant |
| 5,172,702 A | 12/1992 | Leigh et al. |
| 5,183,054 A | 2/1993 | Burkholder et al. |
| 5,188,118 A | 2/1993 | Terwilliger |
| 5,195,533 A | 3/1993 | Chin et al. |
| 5,197,484 A | 3/1993 | Kornberg et al. |
| 5,201,314 A | 4/1993 | Bosley et al. |
| 5,213,110 A | 5/1993 | Kedem et al. |
| 5,224,470 A | 7/1993 | Schnepp-Pesch et al. |
| 5,234,000 A * | 8/1993 | Hakky ............ A61B 10/0275 606/171 |
| 5,240,011 A | 8/1993 | Assa |
| 5,249,582 A | 10/1993 | Taylor |
| 5,249,583 A | 10/1993 | Mallaby |
| 5,250,026 A | 10/1993 | Ehrlich et al. |
| 5,259,837 A | 11/1993 | Van Wormer |
| 5,282,476 A | 2/1994 | Terwilliger |
| 5,284,156 A | 2/1994 | Schramm et al. |
| 5,313,958 A | 5/1994 | Bauer |
| 5,316,013 A | 5/1994 | Striebel, II et al. |
| 5,335,671 A | 8/1994 | Clement |
| 5,335,672 A | 8/1994 | Bennett |
| 5,348,022 A | 9/1994 | Leigh et al. |
| 5,353,804 A | 10/1994 | Kornberg et al. |
| 5,368,045 A | 11/1994 | Clement et al. |
| 5,383,466 A | 1/1995 | Partika |
| 5,385,151 A | 1/1995 | Scarfone et al. |
| 5,392,790 A | 2/1995 | Kanner et al. |
| 5,400,798 A | 3/1995 | Baran |
| 5,415,182 A | 5/1995 | Chin et al. |
| 5,474,075 A | 12/1995 | Goldberg et al. |
| 5,476,101 A | 12/1995 | Schramm et al. |
| 5,490,521 A | 2/1996 | Davis et al. |
| 5,492,130 A * | 2/1996 | Chiou ............ A61B 10/0283 600/566 |
| 5,505,211 A | 4/1996 | Ohto et al. |
| 5,507,298 A | 4/1996 | Schramm et al. |
| 5,515,861 A | 5/1996 | Smith |
| 5,526,822 A | 6/1996 | Burbank et al. |
| D372,310 S | 7/1996 | Hartnett |
| 5,546,957 A | 8/1996 | Heske |
| 5,595,185 A | 1/1997 | Erlich |
| 5,615,690 A | 4/1997 | Giurtino et al. |
| 5,655,542 A | 8/1997 | Weilandt |
| 5,752,923 A | 5/1998 | Terwilliger |
| 5,759,154 A | 6/1998 | Hoyns |
| 5,769,086 A | 6/1998 | Ritchart et al. |
| 5,775,333 A | 7/1998 | Burbank et al. |
| 5,779,647 A | 7/1998 | Chau et al. |
| 5,782,775 A | 7/1998 | Milliman et al. |
| 5,817,033 A | 10/1998 | DeSantis et al. |
| 5,820,554 A | 10/1998 | Davis et al. |
| 5,842,999 A | 12/1998 | Pruitt et al. |
| 5,916,175 A * | 6/1999 | Bauer ............ A61B 10/0275 600/567 |
| 5,921,933 A | 7/1999 | Sarkis et al. |
| 5,921,943 A * | 7/1999 | Kass ............ A61B 10/0275 600/567 |
| 5,928,164 A | 7/1999 | Burbank et al. |
| 5,951,489 A | 9/1999 | Bauer |
| 5,954,670 A | 9/1999 | Baker |
| 5,967,988 A | 10/1999 | Briscoe et al. |
| 5,971,939 A | 10/1999 | DeSantis et al. |
| 5,980,469 A | 11/1999 | Burbank et al. |
| 5,989,196 A | 11/1999 | Chu et al. |
| 5,989,197 A | 11/1999 | Avaltroni |
| 5,993,399 A | 11/1999 | Pruitt et al. |
| 6,007,497 A | 12/1999 | Huitema |
| 6,018,676 A | 1/2000 | Davis et al. |
| 6,077,231 A | 6/2000 | Milliman et al. |
| 6,083,176 A | 7/2000 | Terwilliger |
| 6,086,544 A | 7/2000 | Hibner et al. |
| 6,093,154 A | 7/2000 | Burek et al. |
| 6,106,473 A | 8/2000 | Violante et al. |
| 6,106,484 A | 8/2000 | Terwilliger |
| 6,120,462 A | 9/2000 | Hibner et al. |
| 6,120,463 A | 9/2000 | Bauer |
| 6,162,203 A | 12/2000 | Haaga |
| 6,165,136 A | 12/2000 | Nishtala |
| 6,165,137 A | 12/2000 | Milliman et al. |
| 6,221,029 B1 | 4/2001 | Mathis et al. |
| 6,221,030 B1 | 4/2001 | Avaltroni |
| 6,261,241 B1 | 7/2001 | Burbank et al. |
| 6,273,862 B1 | 8/2001 | Privitera et al. |
| 6,280,399 B1 | 8/2001 | Rossin et al. |
| 6,283,925 B1 | 9/2001 | Terwilliger |
| 6,331,166 B1 | 12/2001 | Burbank et al. |
| 6,346,085 B1 | 2/2002 | Schiffman |
| 6,346,107 B1 | 2/2002 | Cucin |
| 6,358,217 B1 * | 3/2002 | Bourassa ............ A61B 10/0275 600/567 |
| 6,402,701 B1 | 6/2002 | Kaplan et al. |
| 6,428,487 B1 * | 8/2002 | Burdorff ............ A61B 90/361 600/568 |
| 6,436,054 B1 | 8/2002 | Viola et al. |
| 6,471,700 B1 | 10/2002 | Burbank et al. |
| 6,551,253 B2 | 4/2003 | Worm et al. |
| 6,585,664 B2 | 7/2003 | Burdorff et al. |
| 6,592,530 B1 | 7/2003 | Farhadi |
| 6,610,016 B1 | 8/2003 | Violante et al. |
| 6,626,850 B1 | 9/2003 | Chau et al. |
| 6,638,235 B2 | 10/2003 | Miller et al. |
| 6,659,105 B2 | 12/2003 | Burbank et al. |
| 6,689,071 B2 | 2/2004 | Burbank et al. |
| 6,689,072 B2 | 2/2004 | Kaplan et al. |
| 6,723,052 B2 | 4/2004 | Mills |
| 6,749,576 B2 | 6/2004 | Bauer |
| 6,752,768 B2 | 6/2004 | Burdorff et al. |
| D493,532 S | 7/2004 | Levaughn |
| 6,758,824 B1 | 7/2004 | Miller et al. |
| 6,827,692 B2 | 12/2004 | Castellacci |
| 6,860,856 B2 | 3/2005 | Ward et al. |

(56) References Cited

U.S. PATENT DOCUMENTS

| | | | |
|---|---|---|---|
| 6,904,309 B2 | 6/2005 | Derendorf et al. |
| RE38,776 E | 8/2005 | Bauer |
| 6,969,358 B2 | 11/2005 | Baltschun et al. |
| 6,984,213 B2 | 1/2006 | Horner et al. |
| 7,008,382 B2 | 3/2006 | Adams et al. |
| 7,014,610 B2 | 3/2006 | Koulik |
| 7,022,085 B2 | 4/2006 | Cooke et al. |
| 7,022,128 B2 | 4/2006 | Morawski et al. |
| D533,274 S | 12/2006 | Visconti et al. |
| 7,153,274 B2 | 12/2006 | Stephens et al. |
| 7,153,275 B2 | 12/2006 | Blondeau |
| 7,156,815 B2 | 1/2007 | Leigh et al. |
| 7,179,232 B2 | 2/2007 | Sutton et al. |
| 7,189,206 B2 | 3/2007 | Quick et al. |
| 7,226,424 B2 | 6/2007 | Ritchart et al. |
| 7,229,419 B2 | 6/2007 | Hancock |
| 7,278,970 B2 | 10/2007 | Goldenberg |
| 7,329,227 B2 | 2/2008 | Schramm |
| 7,347,829 B2 | 3/2008 | Mark et al. |
| 7,402,140 B2 | 7/2008 | Spero et al. |
| 7,449,000 B2 | 11/2008 | Adams et al. |
| 7,465,278 B2 | 12/2008 | Cicenas et al. |
| 7,468,041 B2 | 12/2008 | Rhodes et al. |
| 7,470,237 B2 | 12/2008 | Beckman et al. |
| 7,479,117 B2 | 1/2009 | Zadow |
| 7,481,775 B2 | 1/2009 | Weikel, Jr. et al. |
| 7,494,473 B2 * | 2/2009 | Eggers | A61B 10/0233 600/568 |
| 7,507,210 B2 | 3/2009 | Hibner et al. |
| D590,502 S | 4/2009 | Geisser et al. |
| 7,517,321 B2 | 4/2009 | McCullough et al. |
| 7,585,282 B2 | 9/2009 | Hancock |
| 7,608,048 B2 | 10/2009 | Goldenberg |
| 7,611,475 B2 | 11/2009 | Spero et al. |
| 7,625,347 B2 | 12/2009 | Burbank et al. |
| 7,628,762 B2 | 12/2009 | Miller et al. |
| 7,645,239 B2 | 1/2010 | Heske et al. |
| 7,648,466 B2 | 1/2010 | Stephens et al. |
| D612,044 S | 3/2010 | Scheibe |
| 7,731,722 B2 | 6/2010 | Lavelle et al. |
| 7,740,598 B2 | 6/2010 | Heske et al. |
| 7,762,961 B2 | 7/2010 | Heske et al. |
| D621,042 S | 8/2010 | Ruf |
| 7,766,843 B2 | 8/2010 | Voegele |
| 7,794,411 B2 | 9/2010 | Ritchart et al. |
| D625,818 S | 10/2010 | Khalil et al. |
| 7,806,835 B2 | 10/2010 | Hibner et al. |
| D628,293 S | 11/2010 | Ruf |
| 7,828,747 B2 | 11/2010 | Heske et al. |
| 7,837,630 B2 | 11/2010 | Nicoson et al. |
| 7,854,706 B2 * | 12/2010 | Hibner | A61B 10/0275 600/568 |
| 7,879,054 B2 | 2/2011 | Gellman et al. |
| 7,883,476 B2 | 2/2011 | Miller et al. |
| 7,905,857 B2 | 3/2011 | Swisher |
| 7,914,464 B2 | 3/2011 | Burdorff et al. |
| 7,938,786 B2 | 5/2011 | Ritchie et al. |
| 7,959,580 B2 | 6/2011 | McCullough et al. |
| 7,963,928 B2 | 6/2011 | Krause |
| 7,988,642 B2 | 8/2011 | Hardin et al. |
| 8,002,713 B2 | 8/2011 | Heske et al. |
| 8,012,102 B2 | 9/2011 | McCullough et al. |
| 8,016,772 B2 | 9/2011 | Heske et al. |
| 8,043,228 B2 | 10/2011 | Cooke et al. |
| 8,048,003 B2 | 11/2011 | Nicoson et al. |
| 8,052,614 B2 | 11/2011 | Heske et al. |
| 8,064,987 B2 | 11/2011 | Carr, Jr. |
| D650,860 S | 12/2011 | Wu |
| 8,088,080 B2 | 1/2012 | Adams et al. |
| 8,109,885 B2 | 2/2012 | Heske et al. |
| 8,137,288 B2 | 3/2012 | Cooke et al. |
| 8,162,850 B2 | 4/2012 | Parihar et al. |
| 8,162,851 B2 | 4/2012 | Heske et al. |
| 8,172,773 B2 | 5/2012 | Heske et al. |
| 8,187,204 B2 | 5/2012 | Miller et al. |
| 8,187,294 B2 | 5/2012 | Miller et al. |
| 8,192,369 B2 | 6/2012 | Bacon et al. |
| 8,197,419 B2 | 6/2012 | Field et al. |
| 8,241,225 B2 | 8/2012 | Seiger et al. |
| 8,246,551 B2 | 8/2012 | Miller et al. |
| 8,251,917 B2 | 8/2012 | Almazan |
| 8,262,586 B2 | 9/2012 | Anderson et al. |
| 8,267,868 B2 | 9/2012 | Taylor et al. |
| 8,277,394 B2 | 10/2012 | Hibner |
| 8,282,574 B2 | 10/2012 | Coonahan et al. |
| 8,287,465 B2 | 10/2012 | Hardin et al. |
| 8,313,463 B2 | 11/2012 | Barrow-Williams et al. |
| 8,328,836 B2 | 12/2012 | Conlon et al. |
| 8,343,070 B2 | 1/2013 | Krueger |
| 8,343,072 B2 | 1/2013 | Bacon et al. |
| 8,357,104 B2 | 1/2013 | Moos et al. |
| 8,382,770 B2 | 2/2013 | DeLegge et al. |
| 8,419,683 B2 | 4/2013 | Miller et al. |
| 8,430,827 B2 | 4/2013 | Nicoson et al. |
| 8,437,834 B2 | 5/2013 | Carr, Jr. |
| 8,500,654 B2 | 8/2013 | Goldenberg |
| 8,506,504 B2 | 8/2013 | Field et al. |
| 8,517,955 B2 | 8/2013 | Keast et al. |
| 8,523,783 B2 | 9/2013 | Cooke et al. |
| 8,529,468 B2 | 9/2013 | Hoffa et al. |
| 8,535,240 B2 | 9/2013 | Flatland et al. |
| 8,562,543 B2 | 10/2013 | Adams et al. |
| 8,562,544 B2 | 10/2013 | Kwon |
| 8,597,200 B2 | 12/2013 | Flatland et al. |
| 8,597,204 B2 | 12/2013 | Flatland et al. |
| 8,597,205 B2 | 12/2013 | Seiger et al. |
| 8,617,079 B2 | 12/2013 | Mitchell |
| D699,348 S | 2/2014 | Morejon |
| 8,656,928 B2 | 2/2014 | Carlson et al. |
| 8,657,760 B2 | 2/2014 | Neoh |
| 8,690,793 B2 * | 4/2014 | Ranpura | A61B 10/0275 600/568 |
| 8,702,621 B2 | 4/2014 | McCullough et al. |
| 8,702,622 B2 | 4/2014 | McCullough et al. |
| 8,721,563 B2 | 5/2014 | Taylor et al. |
| 8,728,003 B2 | 5/2014 | Taylor et al. |
| 8,728,004 B2 | 5/2014 | Heske et al. |
| 8,734,363 B2 | 5/2014 | Bacon |
| 8,771,297 B2 | 7/2014 | Miller et al. |
| 8,834,417 B2 | 9/2014 | Moos et al. |
| 8,845,547 B2 | 9/2014 | Heske et al. |
| 8,858,464 B2 | 10/2014 | Hoffa et al. |
| 8,911,461 B2 | 12/2014 | Traynor et al. |
| 8,951,208 B2 | 2/2015 | Almazan |
| 8,951,209 B2 | 2/2015 | Heske et al. |
| 8,961,430 B2 | 2/2015 | Coonahan et al. |
| 8,968,210 B2 | 3/2015 | Mugan et al. |
| 8,968,211 B2 | 3/2015 | Ferree et al. |
| 8,992,440 B2 | 3/2015 | Reuber et al. |
| 8,998,848 B2 | 4/2015 | Miller et al. |
| D737,440 S | 8/2015 | Shabaz |
| 9,968,337 B2 * | 5/2018 | Haselby | A61B 10/0233 |
| 9,968,338 B2 | 5/2018 | Shabaz |
| 2004/0133124 A1 | 7/2004 | Bates et al. |
| 2004/0167429 A1 | 8/2004 | Roshdieh et al. |
| 2004/0186393 A1 * | 9/2004 | Leigh | A61B 10/0275 600/567 |
| 2005/0004559 A1 * | 1/2005 | Quick | A61B 10/02 606/1 |
| 2005/0075580 A1 | 4/2005 | Leigh et al. |
| 2005/0124914 A1 * | 6/2005 | Dicarlo | A61B 10/0275 606/167 |
| 2006/0130338 A1 | 6/2006 | Dzubak et al. |
| 2006/0195044 A1 | 8/2006 | Cooke et al. |
| 2006/0247530 A1 | 11/2006 | Hardin, Jr. et al. |
| 2006/0271082 A1 | 11/2006 | Kirchhevel et al. |
| 2006/0276747 A1 | 12/2006 | Moos et al. |
| 2007/0010843 A1 | 1/2007 | Green |
| 2007/0032742 A1 * | 2/2007 | Monson | A61B 10/0266 600/568 |
| 2007/0167868 A1 | 7/2007 | Sauer |
| 2007/0208272 A1 * | 9/2007 | Voegele | A61B 10/0283 600/564 |

(56) References Cited

U.S. PATENT DOCUMENTS

| | | | |
|---|---|---|---|
| 2008/0195066 A1* | 8/2008 | Speeg | A61B 10/0275 604/326 |
| 2008/0200836 A1* | 8/2008 | Speeg | A61B 10/0266 600/567 |
| 2008/0214955 A1* | 9/2008 | Speeg | A61B 10/0275 600/567 |
| 2009/0088663 A1 | 4/2009 | Miller et al. | |
| 2009/0118641 A1 | 5/2009 | Van Dam et al. | |
| 2009/0209853 A1 | 8/2009 | Parihar et al. | |
| 2009/0247900 A1 | 10/2009 | Zimmer | |
| 2009/0264794 A1 | 10/2009 | Kodama | |
| 2009/0326413 A1 | 12/2009 | Hancock | |
| 2010/0042014 A1 | 2/2010 | Djordjevic et al. | |
| 2010/0069790 A1 | 3/2010 | Green | |
| 2010/0280408 A1 | 11/2010 | Rusnak | |
| 2011/0125054 A1 | 5/2011 | Clements et al. | |
| 2011/0152715 A1* | 6/2011 | Delap | A61B 10/0275 600/566 |
| 2011/0190660 A1 | 8/2011 | Levy | |
| 2012/0022397 A1 | 1/2012 | Jarial | |
| 2012/0095366 A1 | 4/2012 | Heske et al. | |
| 2012/0116248 A1 | 5/2012 | Mcweeney et al. | |
| 2012/0130275 A1 | 5/2012 | Chudzik et al. | |
| 2012/0245486 A1 | 9/2012 | Melchiorri et al. | |
| 2012/0253230 A1 | 10/2012 | Williams et al. | |
| 2013/0023789 A1 | 1/2013 | Anderson et al. | |
| 2013/0023790 A1 | 1/2013 | Schaeffer | |
| 2013/0053725 A1 | 2/2013 | Beck et al. | |
| 2013/0079665 A1 | 3/2013 | Hibner et al. | |
| 2013/0090570 A1 | 4/2013 | Krueger | |
| 2013/0096458 A1 | 4/2013 | Schraga | |
| 2013/0116594 A1 | 5/2013 | Callede et al. | |
| 2013/0331734 A1 | 12/2013 | Keast et al. | |
| 2015/0080761 A1* | 3/2015 | Schwindt | A61B 10/0283 600/567 |
| 2015/0105690 A1* | 4/2015 | Hathaway | A61B 10/0283 600/566 |
| 2015/0230779 A1* | 8/2015 | Burdorff | A61B 90/361 600/568 |
| 2015/0289857 A1* | 10/2015 | Hatta | A61B 10/0283 600/563 |

FOREIGN PATENT DOCUMENTS

| | | |
|---|---|---|
| WO | 03077767 A1 | 9/2003 |
| WO | 03077768 A1 | 9/2003 |
| WO | 2004086977 A1 | 10/2004 |
| WO | 2004086978 A1 | 10/2004 |
| WO | 2005072621 A1 | 8/2005 |
| WO | 2006022699 A1 | 3/2006 |
| WO | 2006083770 A2 | 8/2006 |
| WO | 2007021904 A2 | 2/2007 |
| WO | 2007021905 A2 | 2/2007 |
| WO | 2008024684 A2 | 2/2008 |
| WO | 2008051987 A2 | 5/2008 |
| WO | 2009085821 A2 | 7/2009 |
| WO | 2013082259 A1 | 6/2013 |
| WO | 2013158072 A1 | 10/2013 |
| WO | 2014081812 A1 | 5/2014 |

* cited by examiner

CORE NEEDLE BIOPSY DEVICE

CROSS-REFERENCE TO RELATED APPLICATIONS

This application is a continuation of U.S. patent application Ser. No. 15/895,116, filed Feb. 13, 2018, is a continuation of U.S. patent application Ser. No. 14/432,650, filed Mar. 31, 2017, now U.S. Pat. No. 9,968,338, which is a U.S. national phase of International Application No. PCT/US2013/070975, filed Nov. 20, 2013, which claims priority to U.S. Provisional Patent Application Ser. No. 61/729,245 entitled "CORE NEEDLE BIOPSY DEVICE" filed Nov. 21, 2012, and U.S. Provisional Patent Application Ser. No. 61/774,293 entitled "CORE NEEDLE BIOPSY DEVICE" filed Mar. 7, 2013, each of which is incorporated herein by reference.

BACKGROUND

1. Field

The present disclosure relates to biopsy devices, and, more particularly, to a handheld core needle biopsy device.

2. Description of the Related Art

Some practitioners that perform biopsy procedures prefer a self-contained handheld biopsy device over that of a large console system. A self-contained handheld biopsy device typically includes a stylet having a pointed distal tip and a side port proximal to the distal tip configured to receive tissue that will be severed to form a tissue sample. The stylet may be in the form of a tube (cannula) or rod. A cutter cannula is positioned coaxial with the stylet to sever the tissue received in the side port of the stylet.

One type of self-contained handheld biopsy devices is a partially disposable biopsy device. A typical partially disposable biopsy device has a reusable handheld driver to which a disposable probe is releasably attached. The reusable handheld driver is typically battery powered, and includes electrical motor drives and an on-board vacuum pump to aid in sample acquisition and/or retrieval. Often, such biopsy devices are configured for single insertion multiple sample (SIMS) procedures. The disposable probe is used on a single patient, and then discarded, while the handheld driver is retained for reuse.

Some attempts have been made to provide a fully disposable biopsy device, which is intended to be discarded in its entirety following use. However, such devices typically have limited capability and/or are not easy to use.

SUMMARY

The present disclosure provides a fully disposable spring powered core needle biopsy device. For user procedural flexibility, a full featured core needle biopsy device of the present invention may include multiple, e.g., two, user selectable firing modes, multiple, e.g., two, user selectable firing distances, and multiple, e.g., dual, sample acquisition triggers. The core needle biopsy device further may be provided in a plurality of different needle gauge size and length combinations. In addition, for ease of use, the core needle biopsy device may utilize a cocking mechanism that reduces the overall force required to cock the device. While the Detailed Description that follows is directed to the structural configuration and operation of a core needle biopsy device of the present disclosure having the full features introduced above, it is contemplated that variations of the core needle biopsy device of the disclosure may include less than all of the features described herein.

The disclosure, in one form, is directed to a biopsy device. The biopsy device includes a cutting cannula mechanism coupled to a sub-frame. The cutting cannula mechanism has a cutting cannula configured to extend along a cannula axis. An inner stylet mechanism is coupled to the sub-frame, and has an inner stylet coaxial with the cutting cannula. A cocking mechanism is configured to cock the cutting cannula mechanism and the inner stylet mechanism by retracting each of the cutting cannula and the inner stylet in a proximal direction to a cocked position. A trigger device is configured to fire at least one of the inner stylet mechanism and the cutting cannula mechanism to advance the respective at least one of the inner stylet and the cutting cannula from the cocked position in a distal direction. A selector assembly includes a selector switch having an exterior tab accessible by a user. The selector assembly is configured to select between at least two user selectable operating modes and at least two user selectable firing distances, wherein a firing distance is the distance of distal travel of each of the inner stylet and the cutting cannula in the distal direction opposite the proximal direction from the cocked position.

The disclosure in another form is directed to a biopsy device. The biopsy device includes a housing defining an interior chamber having a central axis. A sub-frame is positioned in the interior chamber of the housing. The sub-frame has a separator wall and a proximal end wall. The sub-frame is configured to define a distal interior chamber and a proximal interior chamber which are divided by the separator wall. The separator wall has a first lock opening and the proximal end wall has a second lock opening, and the sub-frame has a first rack gear. A cutting cannula mechanism has a cutting cannula, a cutting cannula slider, and a cutting cannula spring. The cutting cannula slider is fixed to a proximal end of the cutting cannula. The cutting cannula slider has a first locking tang configured to selectively engage the first lock opening of the separator wall. The cutting cannula spring is interposed between the cutting cannula slider and the separator wall. A stylet mechanism has an inner stylet slidably received within a lumen of the cutting cannula. An inner stylet slider is fixed to a proximal end of the inner stylet. The inner stylet slider has a second locking tang configured to selectively engage the second lock opening of the proximal end wall. The inner stylet spring is interposed between the inner stylet slider and the end wall. A cocking mechanism includes a cocking slider, a pawl, and a rotary gear. The cocking slider has a second rack gear. The rotary gear is interposed between the first rack gear of the sub-frame and the second rack gear of the cocking slider. The pawl has a proximal end, a distal end and a mid-portion between the proximal end and the distal end. The mid-portion of the pawl is configured to rotatably mount the rotary gear. The pawl is configured to interact with each of the cutting cannula slider and the inner stylet slider.

BRIEF DESCRIPTION OF THE DRAWINGS

The above-mentioned and other features and advantages of this disclosure, and the manner of attaining them, will become more apparent and the disclosure will be better understood by reference to the following description of an embodiment of the disclosure taken in conjunction with the accompanying drawings, wherein:

FIGS. 9A-9D respectively shows for the core needle biopsy device as depicted in FIGS. 1, 3, 5, and 6, the four combinations of the automatic versus semi-automatic firing modes, and the 22 millimeter (mm) versus 11 mm firing distances, with: FIG. 9A showing the selector switch position for the automatic mode, 22 mm throw; FIG. 9B showing the selector switch position for the semi-automatic mode, 22 mm throw; FIG. 9C showing the selector switch position for the semi-automatic mode, 11 mm throw; and FIG. 9D showing the selector switch position for the automatic mode, 11 mm throw.

Corresponding reference characters indicate corresponding parts throughout the several views provided by the Figs. The exemplifications set out herein illustrate an embodiment of the disclosure, and such exemplifications are not to be construed as limiting the scope of the disclosure in any manner.

DETAILED DESCRIPTION

Figure 1:
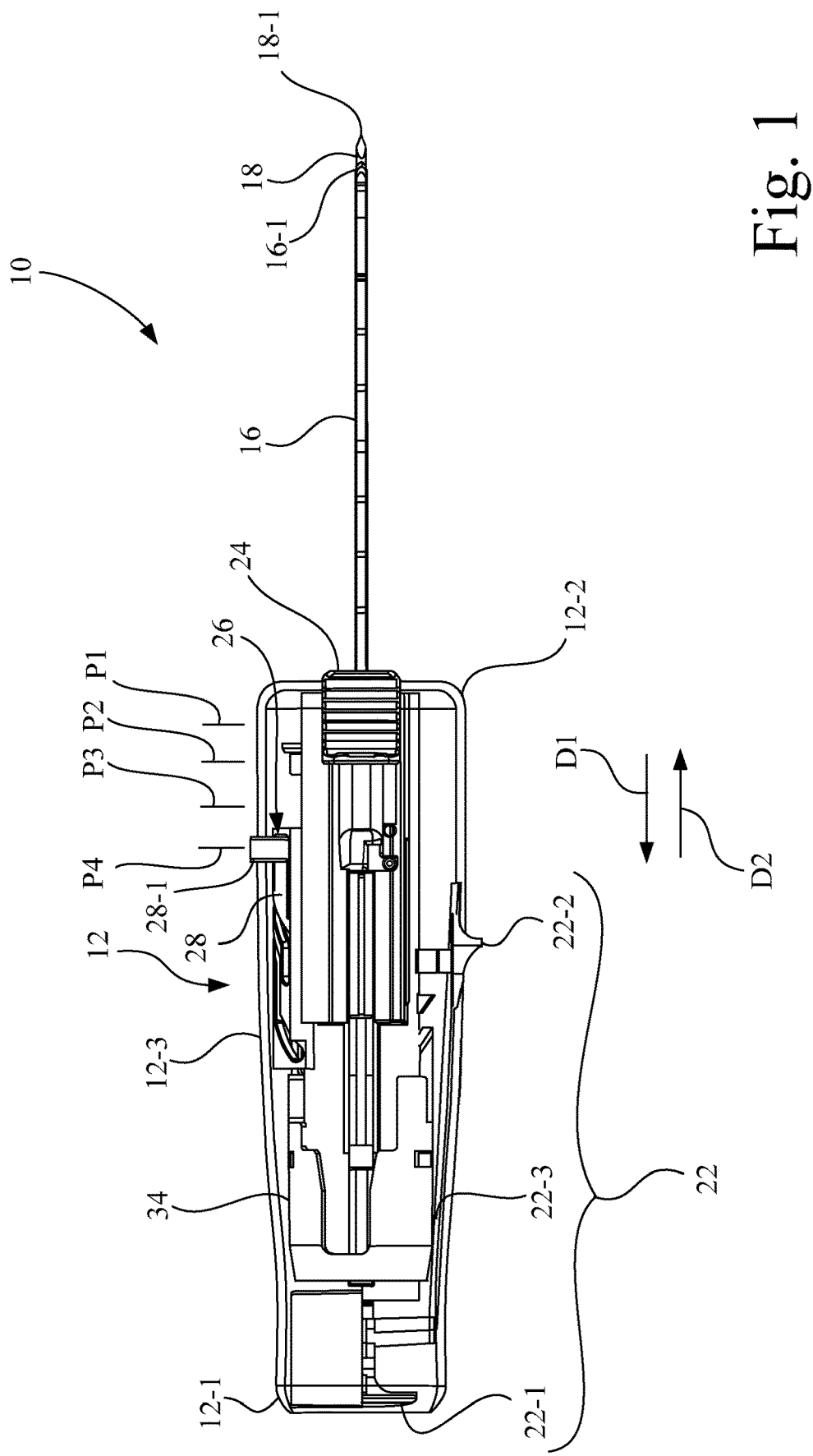
FIG. 1 is a top view of the core needle biopsy device of the present disclosure.
Figure 2:
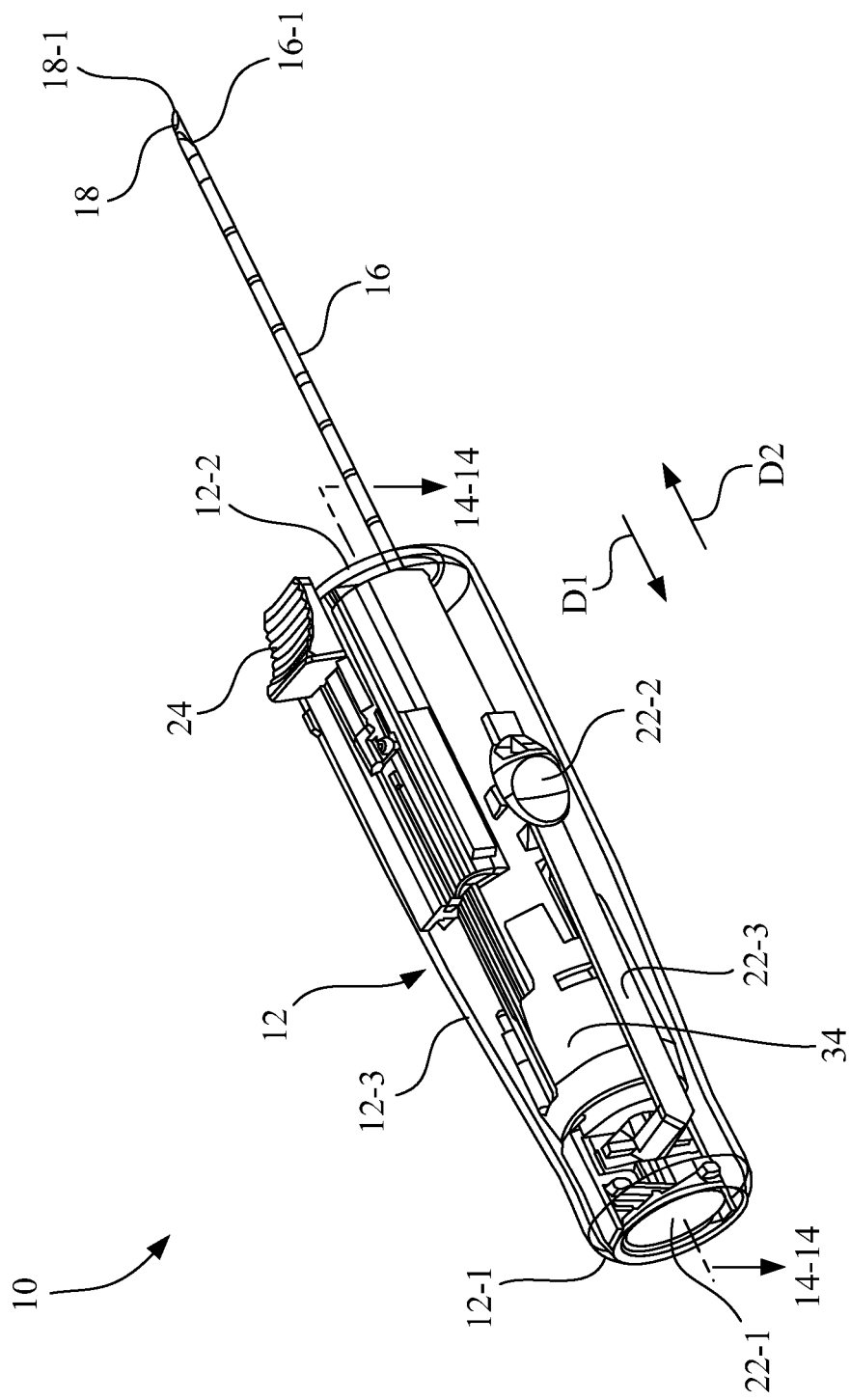
FIG. 2 is a side perspective view of the core needle biopsy device of FIG. 1, with the outer housing shown as transparent.
Figure 3:
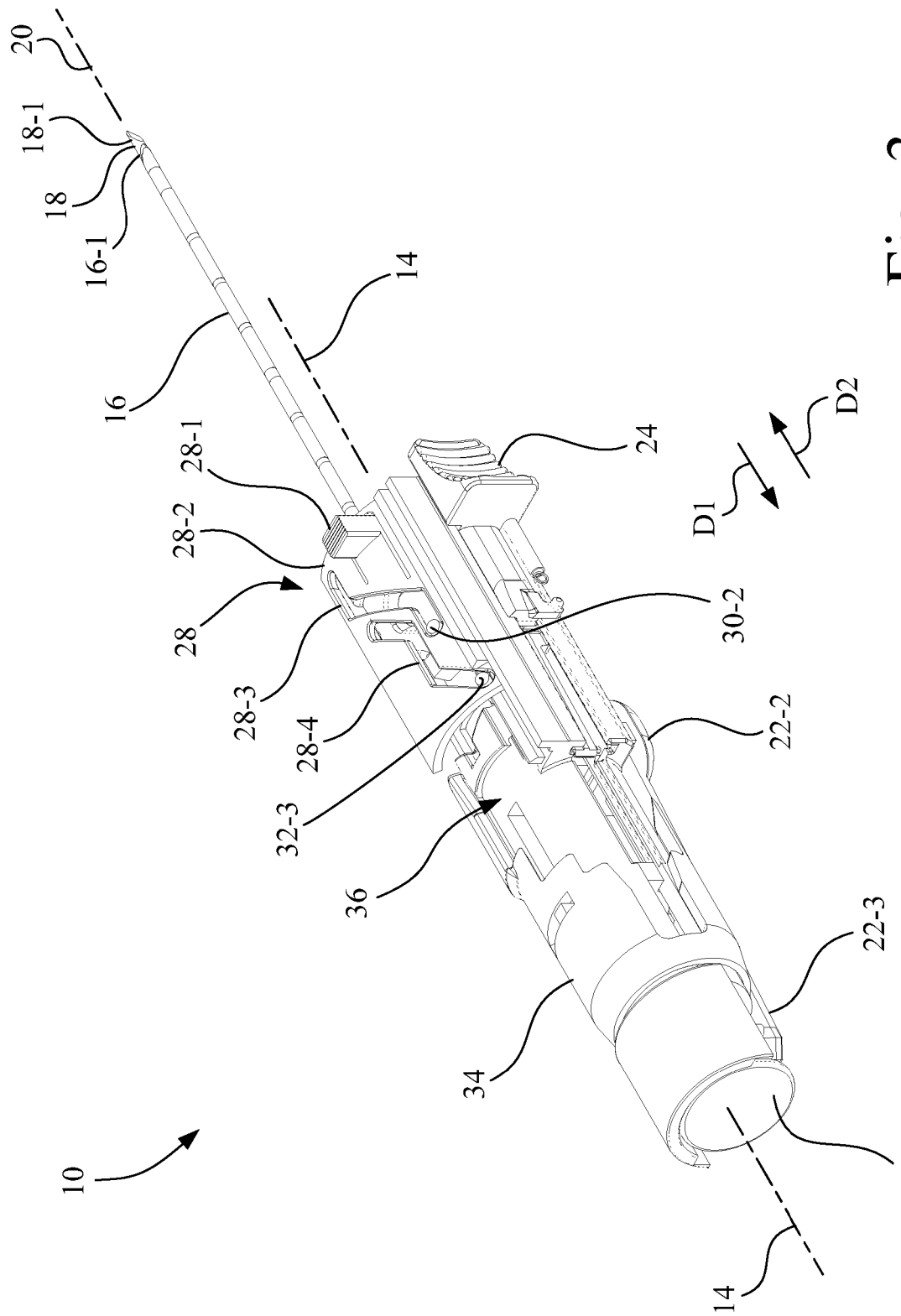
FIG. 3 is a side perspective view of the core needle biopsy device of FIG. 1, with the outer housing removed.
Figure 4:
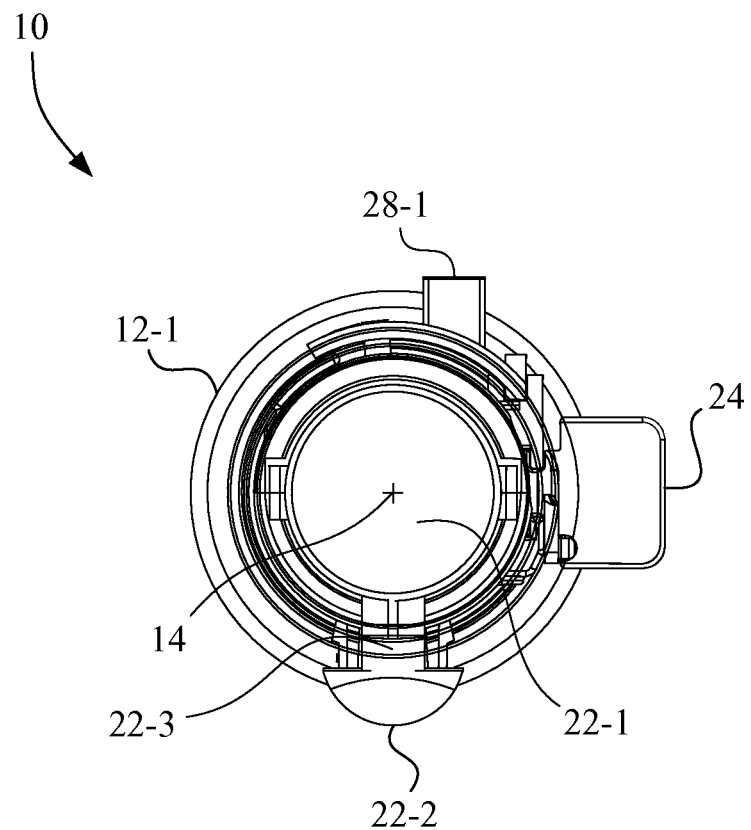
FIG. 4 is a proximal end view of the core needle biopsy device of FIG. 1.

Referring now to the drawings, and more particularly to FIGS. 1-5, there is shown a core needle biopsy device 10 configured in accordance with an embodiment of the present disclosure. Core needle biopsy device 10 includes an outer housing 12 having a proximal end 12-1, a distal end 12-2, and a side wall 12-3. Side wall 12-3 defines an interior chamber 12-4 having a central axis 14. For ease of understanding the disclosure, FIGS. 1 and 2 show core needle biopsy device 10 with outer housing 12 depicted as being transparent, while FIG. 3 shows core needle biopsy device 10 with outer housing 12 removed.

Extending distally from distal end 12-2 of outer housing 12 is a cutting cannula 16 and an inner stylet 18. Inner stylet 18 is slidably received within the lumen of cutting cannula 16, with cutting cannula 16 and inner stylet 18 being coaxial with respect to an axis 20 (see FIG. 3). Axis 20 is parallel to, and radially offset from, central axis 14. Cutting cannula 16 is a hollow elongate member that has a distal beveled cutting edge 16-1. Inner stylet 18 is an elongate member that has a sharp penetrating tip 18-1 and a sample notch 18-2 formed as a side recess proximal to penetrating tip 18-1.

User operational features of core needle biopsy device 10 that are accessible at the exterior of outer housing 12 include a trigger device 22, a cocking slider 24, and a selector assembly 26.

Trigger device 22 includes a rear trigger 22-1 located at the proximal end 12-1 of outer housing 12 and a side trigger 22-2 located along the side wall 12-3 of outer housing 12, such as on the distal top side of the device handle. Rear trigger 22-1 and side trigger 22-2 are connected via an elongate connector bar 22-3. Providing multiple triggers helps to accommodate user preference. Some users, such as radiologists and surgeons may prefer a trigger on the top of the device, such as side trigger 22-2, while others, such as urologist may prefer a trigger on the rear of the device, such as rear trigger 22-1.

Cocking slider 24 is configured to cock the device core needle biopsy device 10 in a two stage process. In a first retraction of cocking slider 24, cutting cannula 16 will be partially retracted in a proximal direction D1 into interior chamber 12-4 and loaded under spring pressure to a cocked position. In a second retraction of cocking slider 24, inner stylet 18 also will be partially retracted in proximal direction D1 into interior chamber 12-4 and loaded under spring pressure to a cocked position.

In the present embodiment, selector assembly 26 is configured to concurrently select between two user selectable firing modes, and to select between two user selectable firing distances. Selector assembly 26 includes a selector switch 28 having an exterior tab 28-1 that is accessible to a user at the exterior of outer housing 12. In the present embodiment, the selectable firing modes are automatic and semi-automatic (sometimes also referred to as manual). Also, in the present embodiment, the two user selectable firing distances are 22 millimeters (mm) and 11 millimeters (mm), as measured from the penetrating tip 18-1 of inner stylet from the cocked position. Exterior tab 28-1 is used to selectively position selector assembly 26 in one of four selector switch positions, labeled in FIG. 1 in sequential order in proximal direction D1 from distal end 12-2 of outer housing 12 toward proximal end 12-1 of outer housing 12: (Position P1) automatic mode, 22 mm throw; (Position P2) semi-automatic mode, 22 mm throw; (Position P3) semi-automatic mode, 11 mm throw; and (Position P4) automatic mode, 11 mm throw.

In the automatic mode, when the user actuates trigger device 22 (one of pressing rear trigger 22-1 or sliding side trigger 22-2 in distal direction D2), inner stylet 18 fires forward in distal direction D2 into the patient by the selected distance (e.g., 22 mm or 11 mm) to the desired location, scooping up tissue in sample notch 18-2. Milliseconds thereafter, cutting cannula 16 is automatically fired forward in distal direction D2 by the selected distance, with the cutting edge 16-1 cutting tissue and with cutting cannula 16 covering over a severed tissue sample within sample notch 18-2. The clinical benefit of firing in automatic mode is a larger sample size compared to firing in a semi-automatic mode. This is because of a slight downward bend in the sample notch 18-2, which, while in motion acts to scoop up tissue during the forward thrust before the cutting cannula 16 is fired immediately thereafter.

In the semi-automatic (manual) mode, when the user actuates trigger device 22 (one of pressing rear trigger 22-1 or sliding side trigger 22-2 in distal direction D2), inner stylet 18 fires forward in distal direction D2 into the patient by the selected distance (e.g., 22 mm or 11 mm) to the desired location. To complete the procedure and fire cutting cannula 16, the user is required to actuate trigger device 22 (one of rear trigger 22-1 or a side trigger 22-2) a second time. The clinical benefit of firing in the semi-automatic mode is a more accurate placement of the inner stylet 18, and in turn sample notch 18-2. By firing only the inner stylet 18 in a first portion of the manual tissue sample collection sequence, the semi-automatic mode allows the user to then reposition inner stylet 18 within the patient prior to collecting the tissue sample such that sample notch 18-2 is directly in the tissue region within the patient where the desired tissue sample is to be taken. When the user is satisfied with the positioning of sample notch 18-2, then the user will actuate trigger device 22 a second time to fire cutting cannula 16 to collect the tissue sample in sample notch 18-2.

The mechanism by which core needle biopsy device 10 effects the selection between the two user selectable firing modes, and between the two user selectable firing distances, is described in further detail below.

Figure 5:
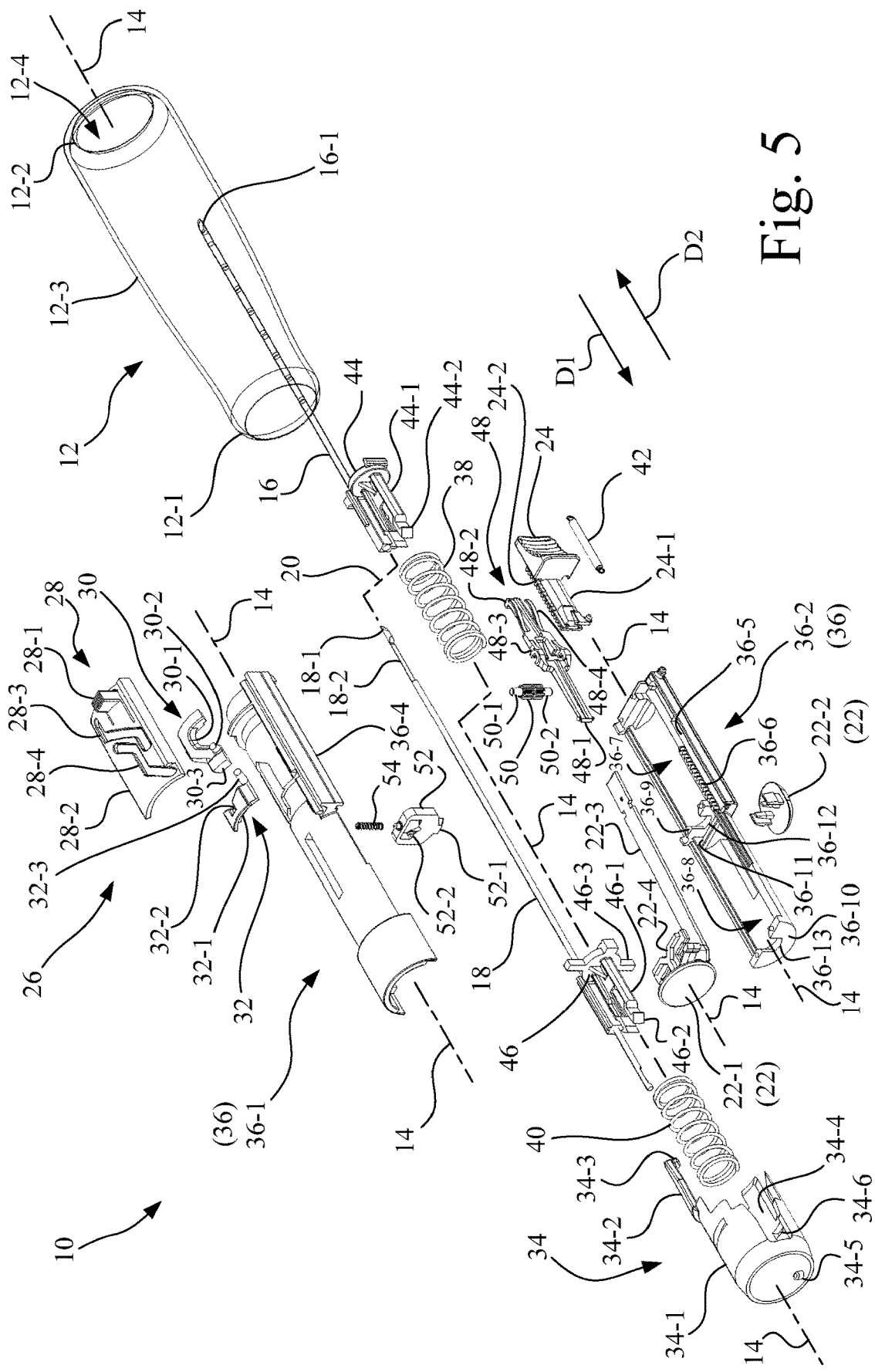
FIG. 5 is an exploded view of the core needle biopsy device depicted in FIGS. 1-4.

Referring also to FIG. 5, selector assembly 26 includes selector switch 28, a selector stop 30, and a selector cam 32. Internal to core needle biopsy device 10, selector assembly 26 is configured to determine a rotational orientation of a sleeve, e.g., a turret, 34, which in turn determines the firing mode and firing distance.

Selector switch 28 includes exterior tab 28-1 which projects upwardly from an arcuate body 28-2. Arcuate body 28-2 includes two cam tracks 28-3 and 28-4. Selector switch 28 provides the user interface for core needle biopsy device 10 to select the firing mode and firing distance.

Selector stop 30 includes a T-shaped body 30-1 having a proximal end 30-3 that has an upwardly extending pin 30-2 configured to engage and ride in cam track 28-3 of selector switch 28. Selector stop 30 is configured to impede the linear motion of sleeve 34 along central axis 14 in distal direction D2 with respect to the selected firing distance selected by selector switch 28.

Selector cam 32 includes a lateral body 32-1 having a shallow V-shaped cam surface with a side notch 32-2 at the apex of the cam surface, and having an upwardly extending pin 32-3. Pin 32-3 is configured to engage and ride in cam track 28-4 of selector switch 28.

Core needle biopsy device 10 further includes a sub-frame 36 formed as a top sub-frame 36-1 and a bottom sub-frame 36-2. As used herein, the terms "top" and "bottom" are used merely as relative terms for ease of explaining the present disclosure. Each of trigger device 22, cocking slider 24 and selector switch 28 is slidably coupled to outer housing 12 and sub-frame 36 for sliding movement in directions D1 or D2.

Figure 6:
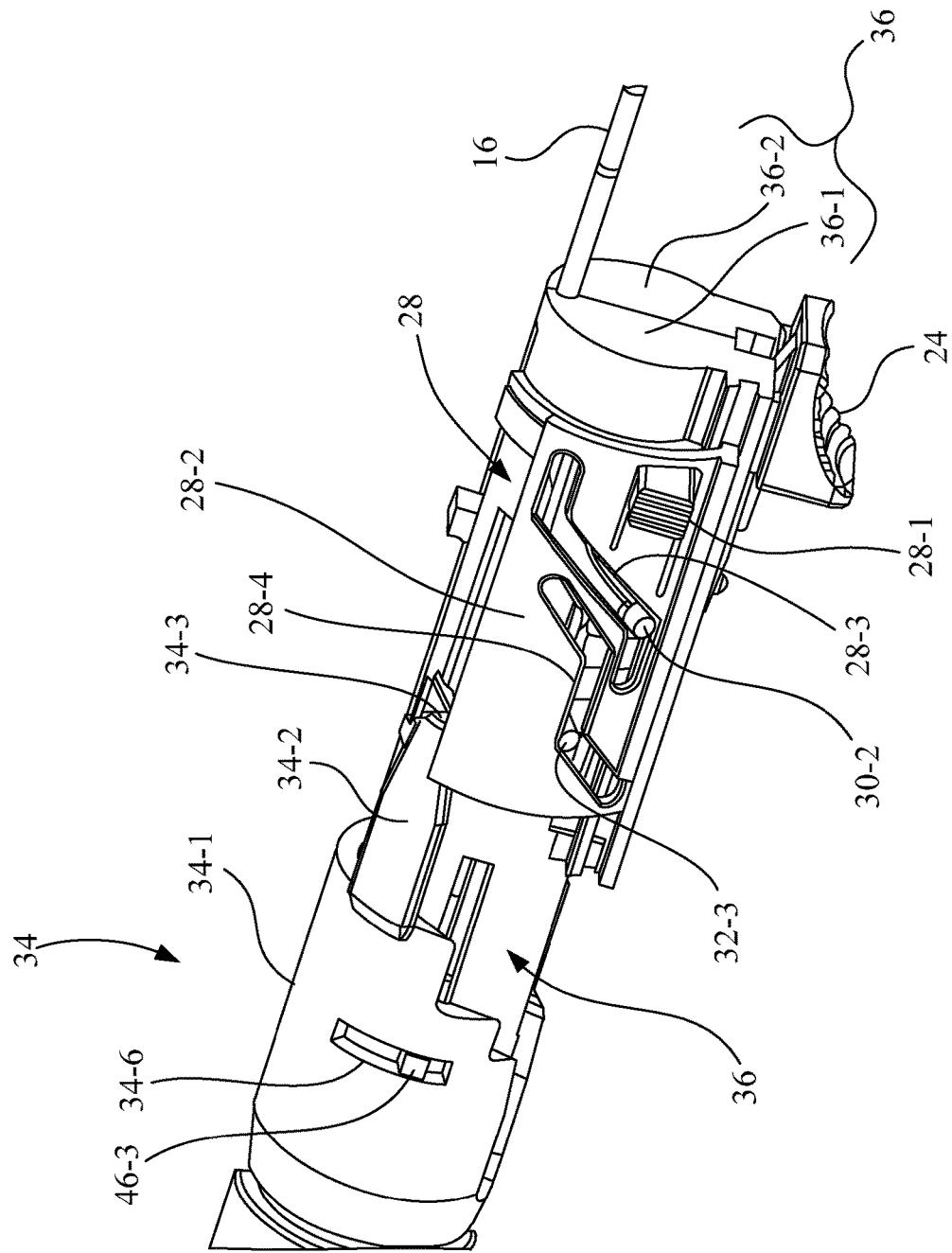
FIG. 6 is a partial side perspective view of the core needle biopsy device as depicted in FIGS. 1, 3 and 5, showing the selector switch assembly for selection between automatic and semi-automatic modes, and for selecting the firing distance.
Figure 7:
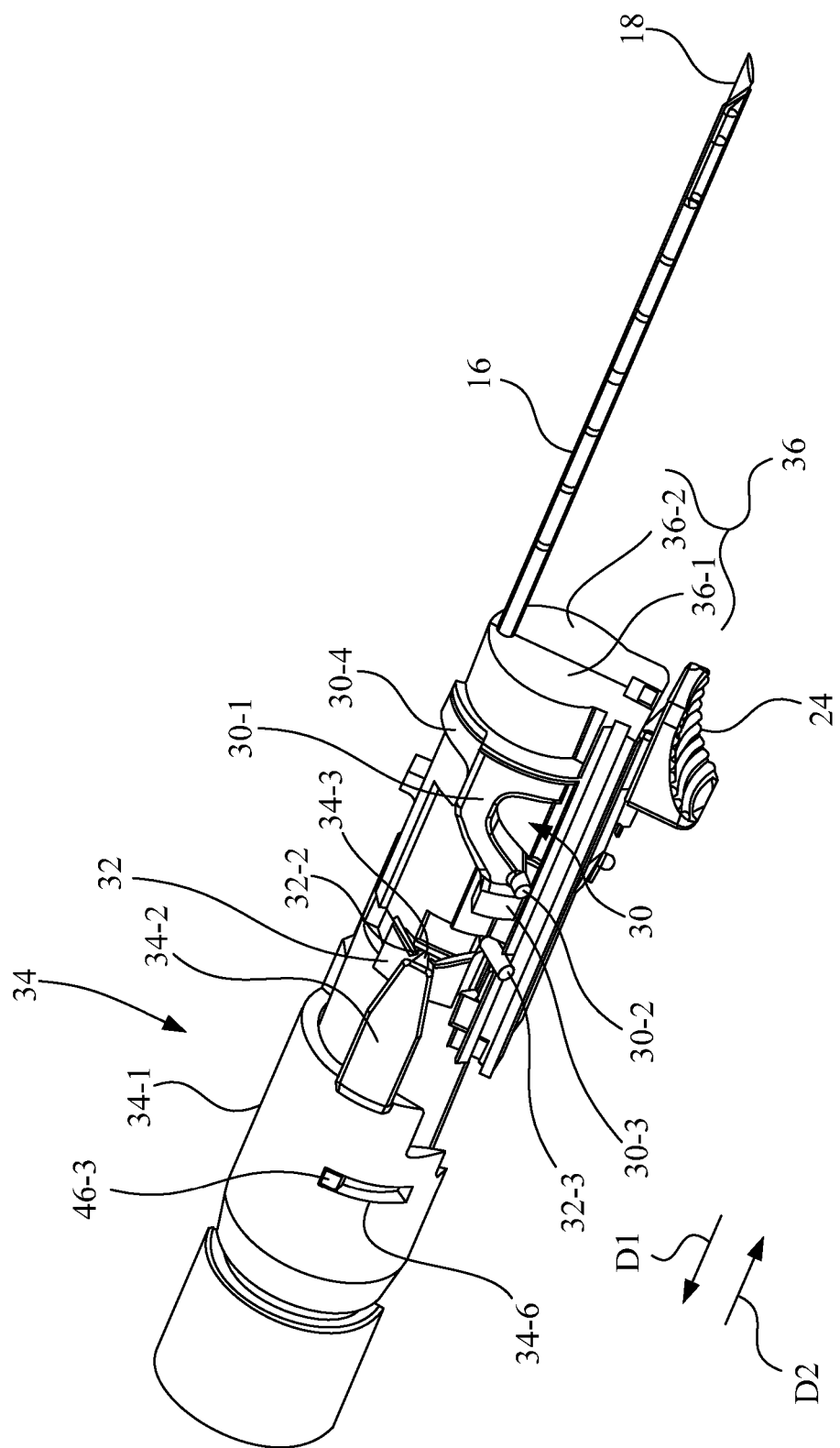
FIG. 7 is a partial side perspective view of the core needle biopsy device as depicted in FIGS. 1, 3 and 6, with the outer cover and selector switch removed to show the selector cam engaged with the sleeve arm.

Referring also to FIGS. 6 and 7, slidably received over sub-frame 36 is sleeve 34. Sleeve 34 is configured as a cylindrical body 34-1 that fits over, and is rotatable with respect to, sub-frame 36. Sleeve 34 has a cantilever arm 34-2 having a downwardly extending pin 34-3. Pin 34-3 is configured to engage the V-shaped cam surface to in turn be guided into side notch 32-2 of selector cam 32. Thus, after core needle biopsy device 10 is cocked, pin 34-3 of sleeve 34 is positioned in side notch 32-2 of selector cam 32, and thus the rotational position of sleeve 34 is determined based on the position (P1, P2, P3, or P4) of selector switch 28 and selector cam 32.

Figure 8:
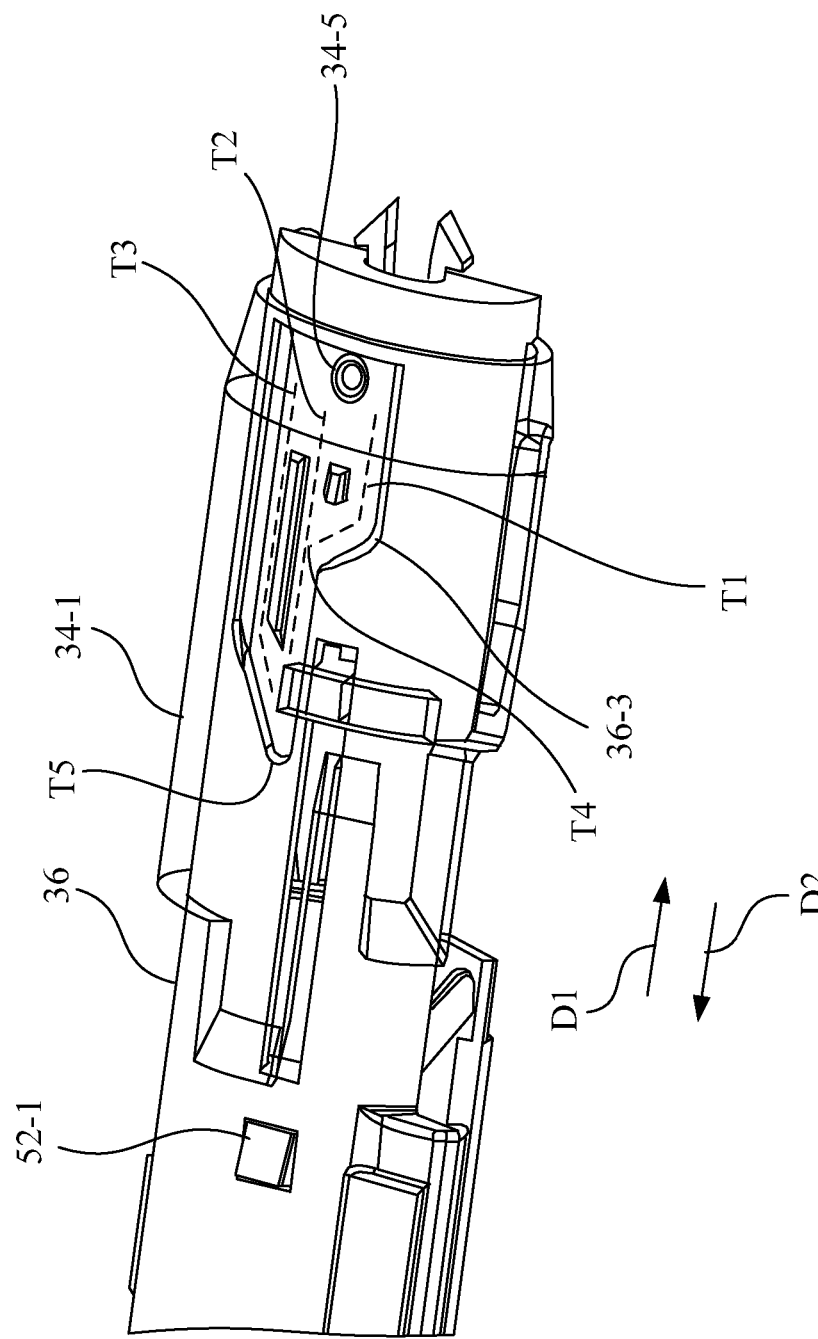
FIG. 8 is a partial side perspective view of the core needle biopsy device as depicted in FIG. 7, with the sleeve shown as transparent, to show the track of the sub-frame and sub-frame track portions that are selectively followed by the sleeve pin.

Referring also to FIG. 8, cylindrical body 34-1 of sleeve 34 has an inner surface 34-4 from which there extends an inwardly facing sleeve pin 34-5. Sleeve pin 34-5 is located in sleeve 34 at a side opposite to that of cantilever arm 34-2 and pin 34-3. In FIG. 8, sleeve 34 is shown as transparent to show sleeve pin 34-5 engaging a track 36-3 of sub-frame 36. In the present embodiment, track 36-3 has three track portions T1, T2, and T3 that are selectively followed by sleeve pin 34-5. The track portion of track 36-3 of sub-frame 36 that sleeve pin 34-5 of sleeve 34 follows in distal direction D2 during firing is determined by the rotational position sleeve 34 as determined by the position (P1, P2, P3, P4) of selector switch 28. Depending on which track portion T1, T2 or T3 that sleeve pin 34-5 of sleeve 34 follows, the sleeve can be toggled into the different firing modes and firing distances, e.g., automatic firing mode versus semi-automatic firing mode, and a 22 mm firing distance versus a 11 mm firing distance.

In particular, track portion T1 corresponds to the automatic mode/11 mm firing distance; track portion T2 corresponds to the semi-automatic mode/both 11 mm and 22 mm firing distances; and track portion T3 corresponds to the automatic mode/22 mm firing distance. Each of the track portions T1 and T2 (11 mm) is configured such that at the end of the respective firing stroke, sleeve 34 is positioned via sleeve pin 34-5 at a common central position T4 corresponding to the terminal end of each of track portions T1 and T2 (11 mm), so as to prepare core needle biopsy device 10 for a subsequent cocking operation. Similarly, each of the track portions T2 (22 mm) and T3 is configured such that at the end of the respective firing stroke, sleeve 34 is positioned via sleeve pin 34-5 at a common central position T5 corresponding to the terminal end of each of track portions T2 (22 mm)

and T3, so as to prepare core needle biopsy device 10 for a subsequent cocking operation.

Figure 9A:
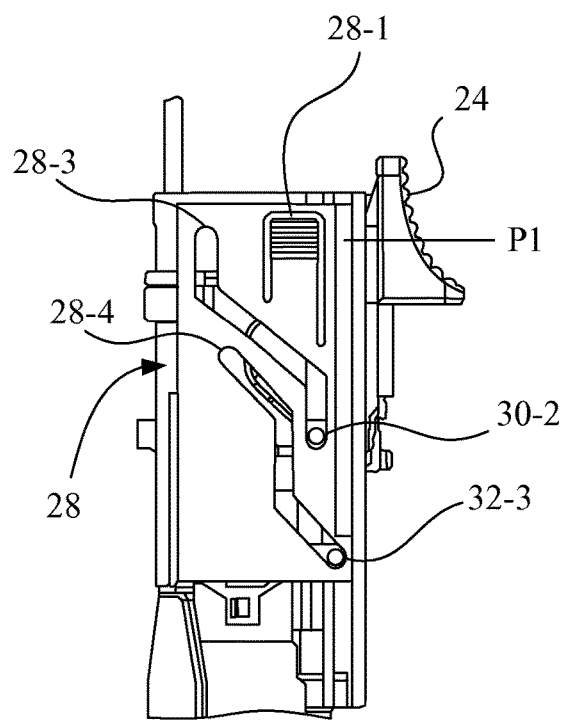
Figure 9B:
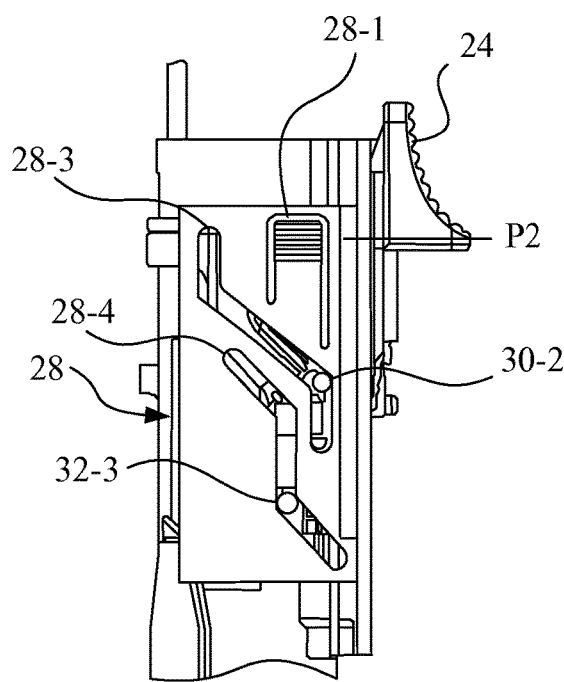
Figure 9C:
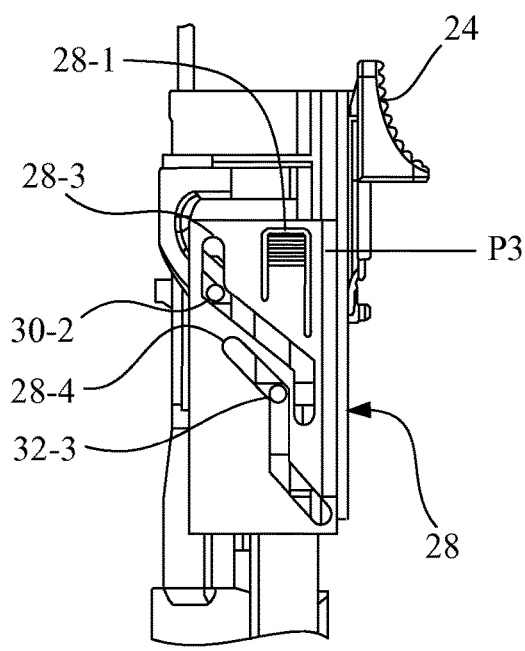
Figure 9D:
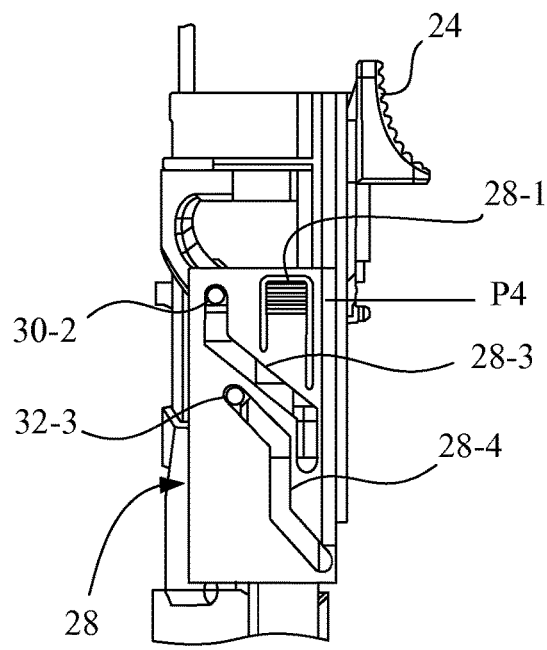

Referring to FIGS. 9A-9D, there is shown a depiction of the selector switch 28 in the selector switch positions: FIG. 9A, (Position P1) automatic mode, 22 mm throw; FIG. 9B, (Position P2) semi-automatic mode, 22 mm throw; FIG. 9C, (Position P3) semi-automatic mode, 11 mm throw; and FIG. 9D, (Position P4) automatic mode, 11 mm throw; and which show the position of pin 30-2 of selector stop 30 relative to cam track 28-3 of selector switch 28, and of pin 32-3 of selector cam 32 relative to cam track 28-4 which in turn is coupled to via pin 34-3 of sleeve 34 via side notch 32-2 of selector cam 32. In the present embodiment, each of the cam tracks 28-3 and 28-4 has three adjoining track segments having end points that correspond to a plurality of mode-distance combinations of the plurality of selector switch positions.

Figure 10:
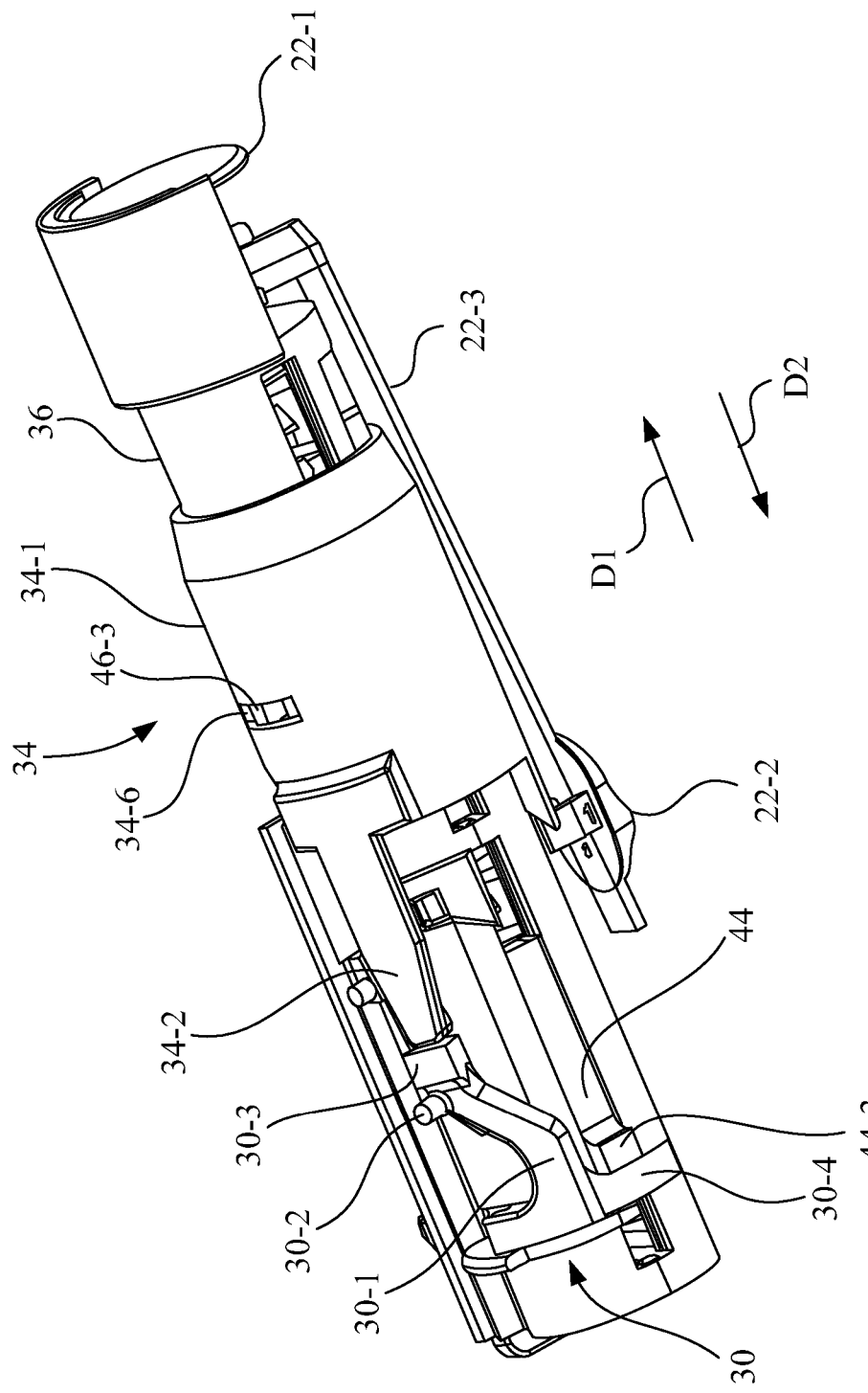
FIG. 10 is a partial side perspective view of the core needle biopsy device as depicted in FIGS. 1 and 5-7, with the outer cover and selector switch removed to show the selector stop of the switch selector assembly engaged with the sleeve at the 11 mm firing distance.

Referring to FIG. 10, the longitudinal travel of sleeve 34 is limited by selector stop 30. In particular, sleeve cantilever arm 34-2 is positioned to abut proximal end 30-3 of selector stop 30, with the position of selector stop 30 being determined by selector switch 28 based on the selected firing distance, e.g., 22 mm or 11 mm.

Figure 11:
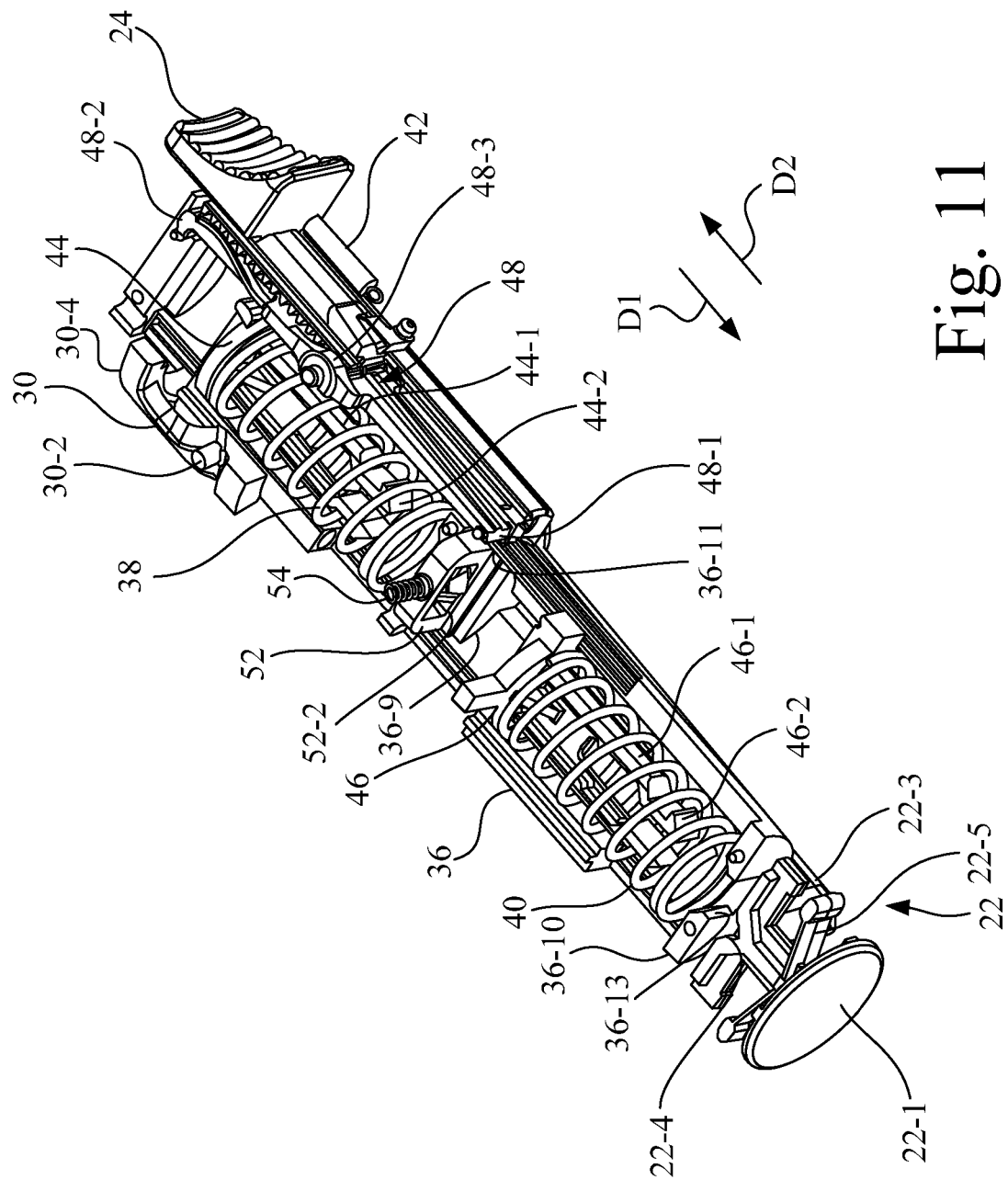
FIG. 11 is a partial perspective view of the core needle biopsy device as depicted in FIGS. 1-3 and 5, with the outer cover and the top half of the core needle biopsy device removed to show the cocking mechanism and firing mechanism at the 11 mm firing distance, in the fired, or pre-cocked, state.
Figure 12:
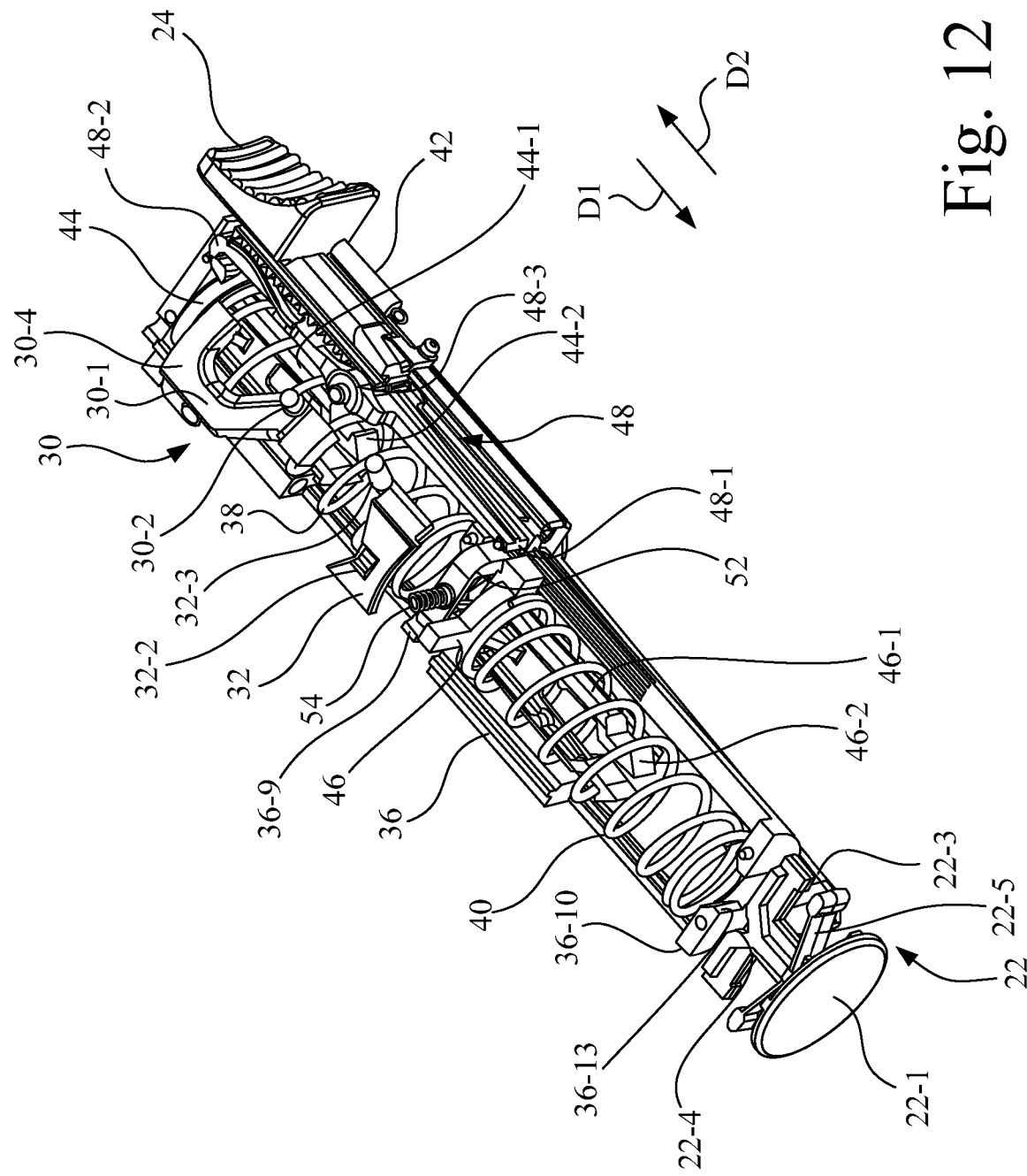
FIG. 12 is a partial perspective view of the core needle biopsy device as depicted in FIGS. 1-3 and 5, with the outer cover and the top half of the core needle biopsy device removed to show the cocking mechanism and firing mechanism at the 22 mm firing distance, in the fired, or pre-cocked, state.
Figure 13:
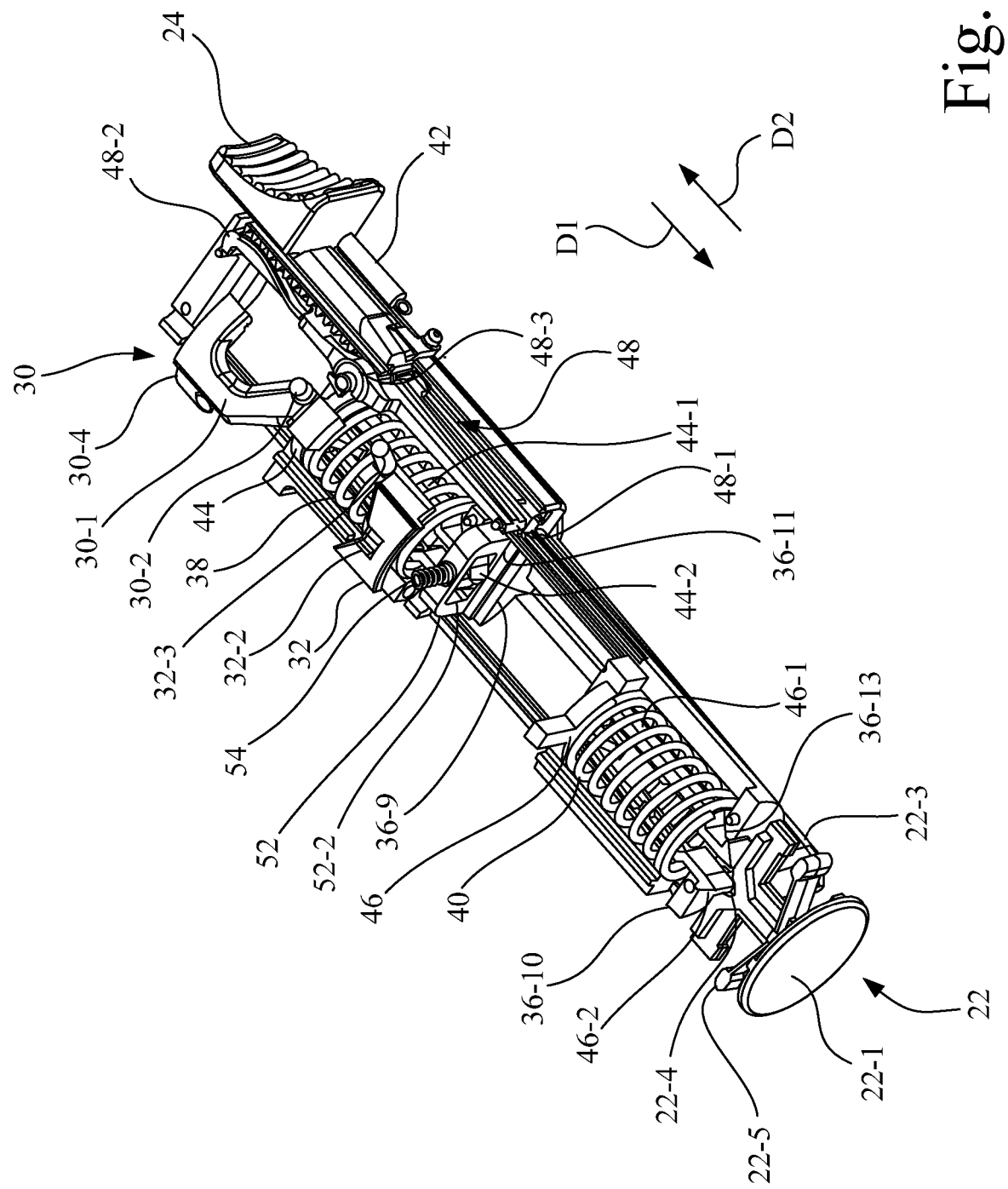
FIG. 13 is a partial perspective view of the core needle biopsy device as depicted in FIGS. 1-3 and 5, with the outer cover and the top half of the core needle biopsy device removed to show the cocking mechanism in the fully cocked state.

Referring also to FIGS. 11-13, the mechanism that effects the cocking of core needle biopsy device 10 in a two stage process is described in further detail below, followed by a description of the mechanism that effects firing of core needle biopsy device 10.

As used herein, "cocking" of core needle biopsy device 10 is the process by which each of cutting cannula spring 38 and inner stylet spring 40 are individually compressed and held in the compressed state (cocked) to store energy that will be released during a firing operation.

In summary, with reference to FIGS. 1, 5, and 11-13, with a first user retraction of cocking slider 24 in proximal direction D1, cutting cannula 16 will be partially retracted in proximal direction D1 into interior chamber 12-4 and cutting cannula spring 38 is compressed and held. A return spring 42 coupled between cocking slider 24 and sub-frame 36 will return cocking slider to its home (start) position after the user releases cocking slider 24. With a second user retraction of cocking slider 24, inner stylet 18 also will be partially retracted in proximal direction D1 into interior chamber 12-4 and inner stylet spring 40 will be cocked and held.

More particularly, the mechanism by which core needle biopsy device 10 effects cocking of device core needle biopsy device 10 includes cocking slider 24, cutting cannula spring 38, inner stylet spring 40, return spring 42, cutting cannula slider 44, inner stylet slider 46, pawl 48, and gear 50. Gear 50 has opposing axel ends 50-1 and 50-2. Axel end 50-1 is received in a longitudinally oriented slot 36-4 in top sub-frame 36-1, and axel end 50-2 is received in a longitudinally oriented slot 36-5 in bottom sub-frame 36-2. Each of top sub-frame 36-1 and bottom sub-frame 36-2 further includes a respective rack gear 36-6 having teeth which engage the teeth of gear 50. Cocking slider 24 includes a longitudinal portion 24-1 having a rack gear 24-2 having teeth which engage the teeth of gear 50. Each of rack gear 36-6 and rack gear 24-2 are simultaneously engaged with gear 50, thus providing a mechanical advantage that reduces the amount of force necessary to move cocking slider 24 to cock core needle biopsy device 10.

Pawl 48 has a proximal end 48-1, a distal end 48-2, and a mid-portion 48-3. Distal end 48-2 is configured as a distal hook member, also referenced as 48-2. Gear 50 is rotatably mounted at axel ends 50-1 and 50-2 to mid-portion 48-3 of pawl 48. Pawl 48 includes one or more leaf springs 48-4 which bias pawl 48 toward cutting cannula slider 44 and inner stylet slider 46 after the user cocks core needle biopsy device 10 the first and second time, respectively. Pawl 48 is driven by the gear 50 and cocking slider 24, and pawl 48 directly interacts with cutting cannula slider 44 and inner stylet slider 46, respectively, to move cutting cannula slider 44 and inner stylet slider 46 to a cocked position where they are locked in place, as further described below.

Cutting cannula slider 44 is fixed to a proximal end of cutting cannula 16. Cutting cannula slider 44 includes a pair of locking tangs 44-1 formed as elongate cantilevered arms having respective outwardly facing latch hooks 44-2 having outer ramped surfaces that diverge in distal direction D2.

Inner stylet slider 46 is fixed to a proximal end of inner stylet 18. Inner stylet slider 46 includes a pair of locking tangs 46-1 formed as elongate cantilevered arms having respective outwardly facing latch hooks 46-2 having outer ramped surfaces that diverge in distal direction D2.

Sub-frame 36 is configured to define a distal interior chamber 36-7 and a proximal interior chamber 36-8, which are divided by a separator wall 36-9, and has an end wall 36-10.

Distal interior chamber 36-7 is configured to receive and support cutting cannula slider 44, with cutting cannula spring 38 being interposed between cutting cannula slider 44 and separator wall 36-9. Separator wall 36-9 includes a lock opening 36-12 configured to receive outwardly facing latch hooks 44-2 of locking tangs 44-1 of cutting cannula slider 44 when cutting cannula slider 44 is moved to the cocked position.

Proximal interior chamber 36-8 is configured to receive and support inner stylet slider 46, with inner stylet spring 40 being interposed between inner stylet slider 46 and end wall 36-10. End wall 36-10 includes a lock opening 36-13 configured to receive the outwardly facing latch hooks 46-2 of locking tangs 46-1 of inner stylet slider 46 when inner stylet slider 46 is moved to the cocked position.

During a cocking procedure, distal hook member 48-2 of pawl 48 is biased by leaf springs 48-4 such that distal hook member 48-2 of pawl 48 is engaged with the distal end of cutting cannula slider 44. A first movement of cocking slider 24 in proximal direction D1 causes a rotation of gear 50, and in turn linear displacement of pawl 48 which in turn pulls cutting cannula slider 44 in proximal direction D1 and compresses cutting cannula spring 38. Once the outwardly facing latch hooks 44-2 of locking tangs 44-1 of cutting cannula slider 44 have passed through lock opening 36-12 of separator wall 36-9 the cocking of cutting cannula slider 44, and in turn cutting cannula 16, is complete and cocking slider 24 may be released to return to its home (start) position by the biasing effects of return spring 42.

With cutting cannula slider 44 now in the cocked position, once cocking slider 24 has returned to its distal home position, proximal end 48-1 of pawl 48 is biased by a third leaf spring (not shown) on the opposite side of pawl 48 from leaf springs 48-4, such that proximal end 48-1 of pawl 48 is positioned to engage the distal end of inner stylet slider 46. A second movement of cocking slider 24 in proximal direction D1 causes a rotation of gear 50, and in turn effects linear displacement of pawl 48 which in turn pushes inner stylet slider 46 in proximal direction D1 and compresses inner stylet spring 40. Once the outwardly facing latch hooks 46-2 of locking tangs 46-1 of inner stylet slider 46 have passed through lock opening 36-13 of end wall 36-10, the cocking of inner stylet slider 46, and in turn inner stylet 18, is complete and cocking slider 24 may be release to return to its home (start) position by the biasing effects of return spring 42.

Once cocked, the firing mode and firing distance is selected by selector switch 28.

Referring again to FIG. 10, the longitudinal travel of sleeve 34 is limited by selector stop 30, with the position of selector stop 30 being determined by selector switch 28 based on the selected firing distance, e.g., 22 mm or 11 mm. In particular, with the 11 mm firing distance selected, sleeve 34 is rotationally positioned such that sleeve cantilever arm 34-2 is positioned to abut proximal end 30-3 of selector stop 30 as sleeve 34 is moved in distal direction D2. In addition, the longitudinal travel limit of cutting cannula slider 44 is also limited by selector stop 30. In particular, cutting cannula slider 44 includes a lower tab 44-3 that is positioned to abut the distal T-shaped portion 30-4 of selector stop 30. Further, an arcuate slot 34-6 in sleeve 34 is configured to engage a lower tab 46-3 of inner stylet slider 46, such that sleeve 34 and inner stylet slider 46 will move longitudinally together, while sleeve 34 is free to rotate about central axis 14 independent of the rotationally stationary inner stylet slider 46.

Figure 14:
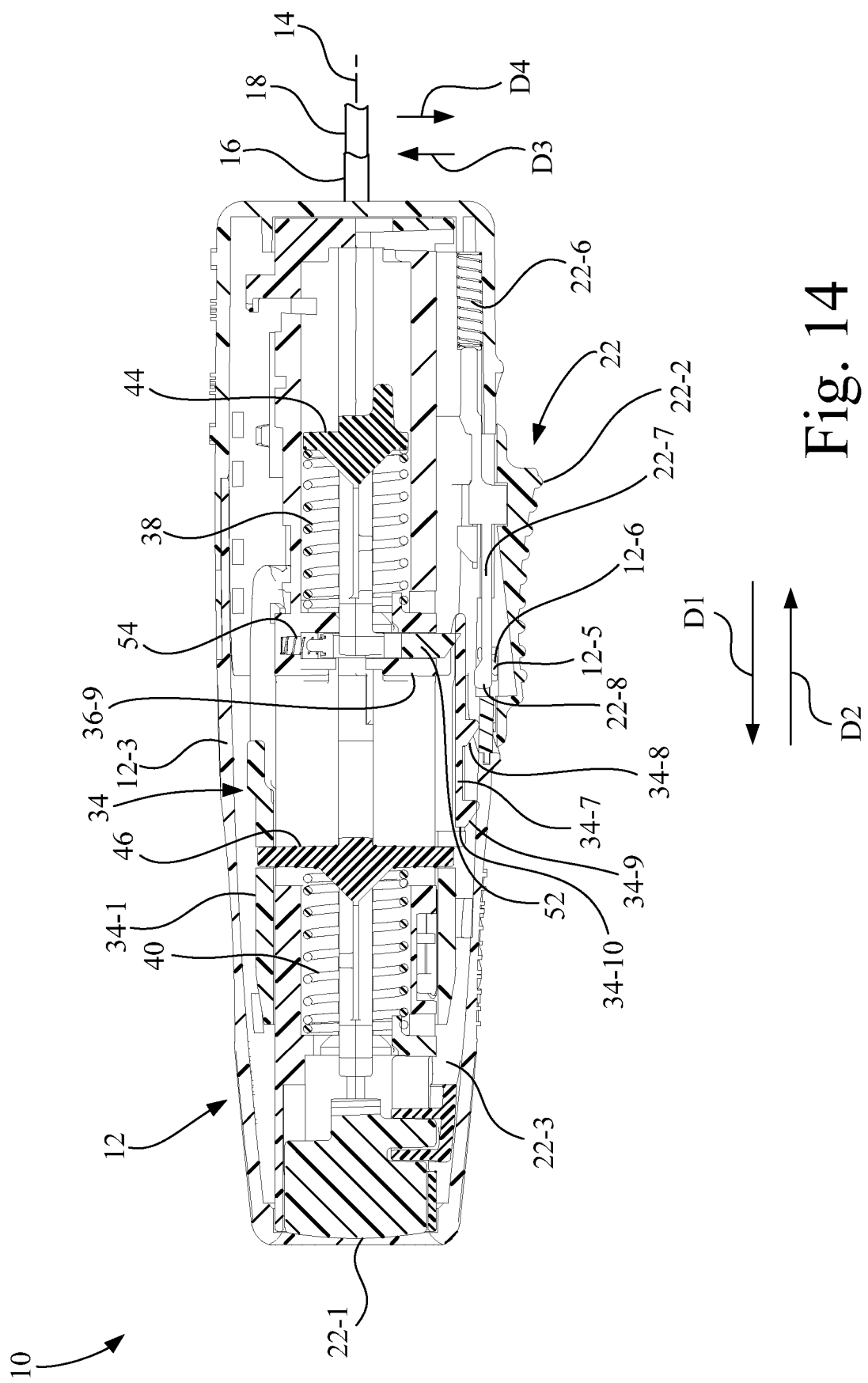
FIG. 14 is a section view of the core needle biopsy device of FIG. 2 taken along plane 14-14, showing the core needle biopsy device in the fully cocked state.

The mechanism by which core needle biopsy device 10 effects firing is described below with respect to FIGS. 13-17. FIGS. 13 and 14 show core needle biopsy device 10 as being fully cocked and ready for firing, i.e., both the cutting cannula slider 44 and the inner stylet slider 46 are restrained in the cocked position, with the respective cutting cannula spring 38 and inner stylet spring 40 being compressed.

Trigger device 22 includes a wedge shaped void 22-4. When fully cocked, and in either of the automatic mode or semi-automatic mode, actuating trigger device 22 (pressing rear trigger 22-1 in distal direction D2, or sliding side trigger 22-2 in distal direction D2) a first time causes wedge shaped void 22-4 of trigger device 22 to engage (e.g., squeeze) the outer ramped surfaces of outwardly facing latch hooks 46-2 of locking tangs 46-1 of inner stylet slider 46 to compress and release locking tangs 46-1 from the lock opening 36-13 in end wall 36-10, thus permitting the pre-compressed inner stylet spring 40 to decompress to fire inner stylet slider 46, and in turn inner stylet 18, in distal direction D2 at a rapid velocity.

Trigger device 22 may optionally include a leaf return spring 22-5 positioned proximal to wedge shaped void 22-4, which may be configured as a pair of diametrically opposed cantilever arms that are positioned to engage a portion of proximal end 12-1 of outer housing 12. As such, when trigger device 22 is moved by the user in the distal direction D2, and then released, trigger device 22 is returned to its proximal (home) position by the biasing action of leaf return spring 22-5. Alternatively, the optional leaf return spring 22-5 may be replaced by, or supplemented with, a coil return spring 22-6 (see FIG. 14).

Referring now to FIGS. 5 and 13-15B, located between cutting cannula slider 44 and inner stylet slider 46 is a strike piece 52, which is configured to release the locking tangs 44-1 on cutting cannula slider 44. The strike piece 52 includes a ramped protrusion 52-1 and a ramped opening 52-2. When cocked as shown in FIGS. 13 and 14, ramped protrusion 52-1 perpendicularly extends through a slide channel opening 36-11 in bottom sub-frame 36-2.

In the automatic mode, when the inner stylet slider 46 is fired the sleeve 34 also moves concurrently in the distal direction D2 along one of track portions T1 and T3 (see FIG. 8). When inner stylet slider 46 is near (e.g., within a range of 0 to 2 mm) the end of its stroke in distal direction D2, sleeve 34 engages and depresses strike piece 52, which causes strike piece 52 to move inwardly perpendicular to central axis 14 and axis 20 against the biasing force of spring 54. At this time, ramped opening 52-2 of strike piece 52 engages (e.g., squeezes) the outer ramped surfaces of outwardly facing latch hooks 44-2 of locking tangs 44-1 of cutting cannula slider 44 to compress, e.g., radially displace, and release locking tangs 44-1 from lock opening 36-12 in separator wall 36-9, thus permitting the pre-compressed cutting cannula spring 38 to decompress to fire cutting cannula slider 44, and in turn cutting cannula 16, in distal direction D2 at a rapid velocity.

Figure 15A:
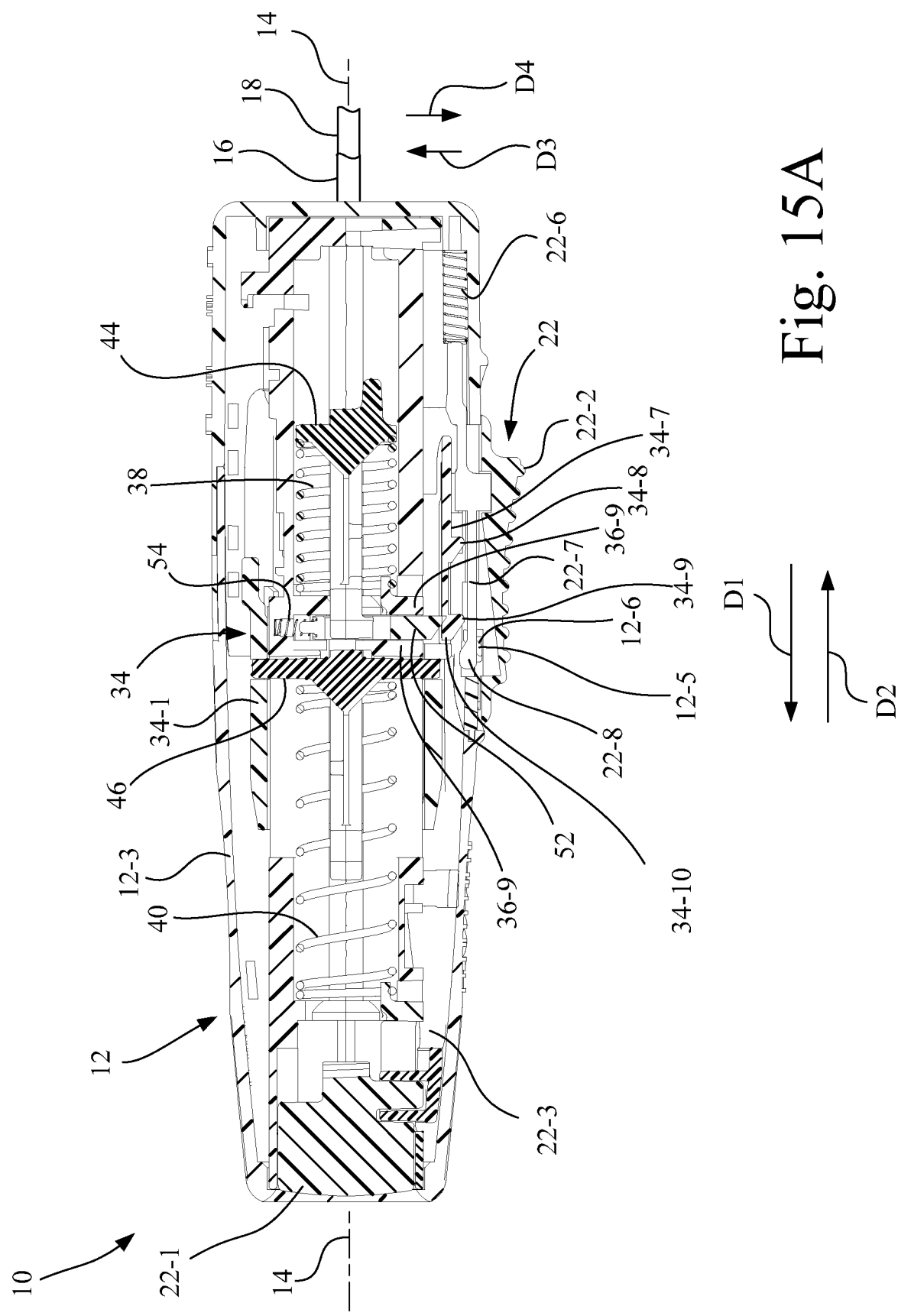
FIG. 15A is a section view of the core needle biopsy device corresponding to FIG. 14 after the stylet has been fired, and with the cutting cannula in the cocked state.
Figure 15B:
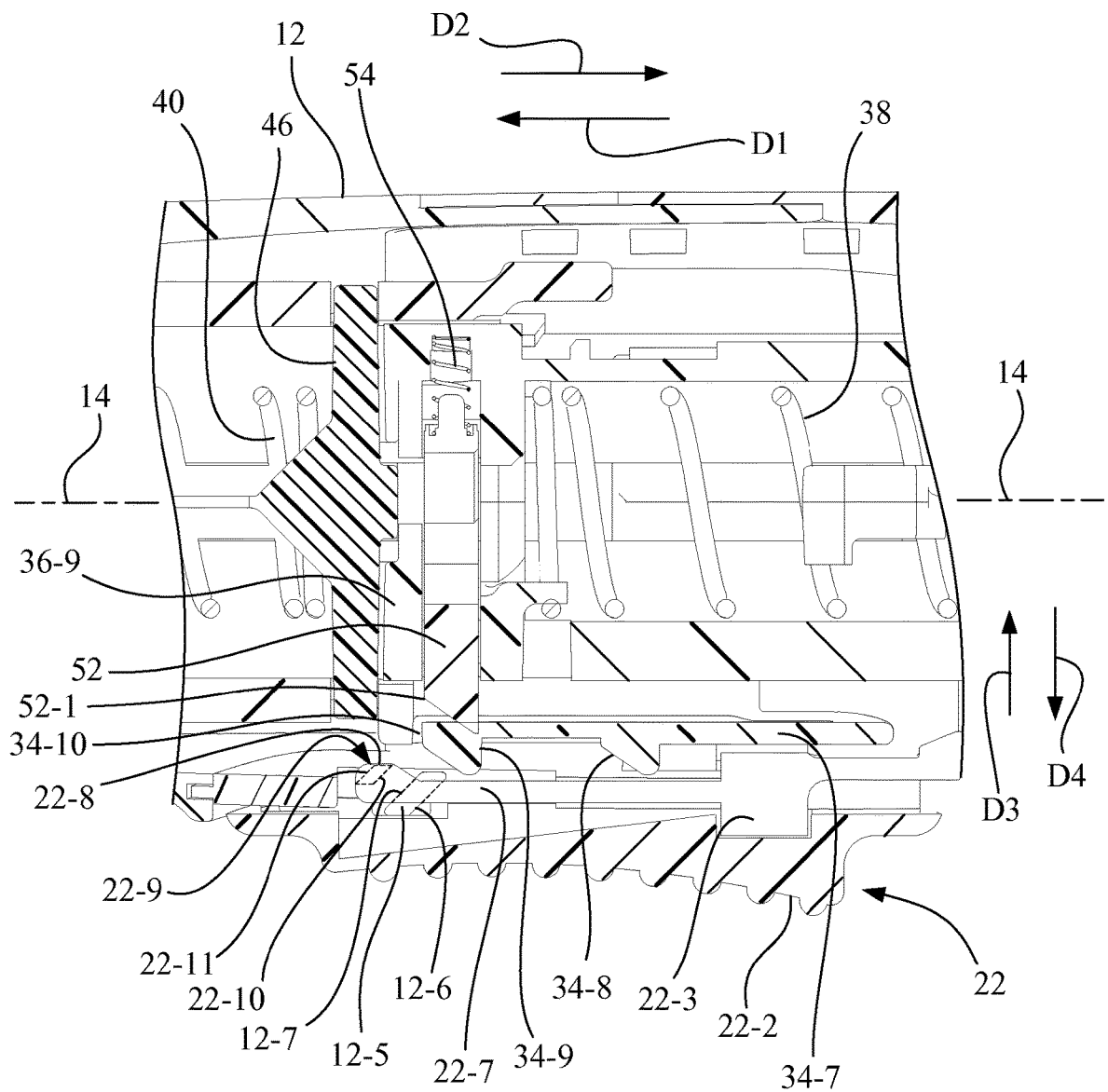
FIG. 15B is an enlarged central portion of the section view of FIG. 15A showing details of the semi-automatic trigger mechanism that facilitates the firing of the cutting cannula.

The semi-automatic mode will be described with specific reference to FIGS. 5, 15A, 15B and 16. Based on the prior selection of the semi-automatic mode, sleeve 34 has been rotated to a center position corresponding to track T2 (see FIG. 8) to prevent sleeve 34 from depressing strike piece 52 near or at the end of the firing stroke of inner stylet slider 46 (see FIGS. 15A and 15B). As such, as shown in FIGS. 15A and 15B, cutting cannula slider 44 remains cocked with cutting cannula spring 38 remaining in the compressed condition.

Thus, in the semi-automatic mode following the firing of the inner stylet slider 46, cutting cannula slider 44 remains cocked with cutting cannula spring 38 remaining in the compressed condition, awaiting a second actuation of trigger device 22. In general, in the semi-automatic mode, strike piece 52 is depressed by the second actuation of trigger device 22, which likewise causes strike piece 52 to move in direction D3 inwardly perpendicular to central axis 14, and axis 20, at which time ramped opening 52-2 of strike piece 52 engages the outer ramped surfaces of outwardly facing latch hooks 44-2 of locking tangs 44-1 of cutting cannula slider 44 to compress, e.g., radially displace, and release locking tangs 44-1 from lock opening 36-12 in separator wall 36-9, thus permitting the pre-compressed cutting cannula spring 38 to decompress to fire cutting cannula slider 44, and in turn cutting cannula 16, in distal direction D2 at a rapid velocity.

The semi-automatic trigger mechanism for effecting the firing of cutting cannula slider and cutting cannula 16 as a result of the second trigger actuation in the semi-automatic mode will now be described with reference to FIGS. 14-17.

Sleeve 34, discussed above, further includes a proximally extending cantilever arm 34-7 having a pair of longitudinally spaced ramped protrusions 34-8, 34-9. Ramped protrusion 34-8 corresponds to semi-automatic operation at the 11 mm firing distance, and ramped protrusion 34-9 corresponds to the semi-automatic operation at the 22 mm firing distance. Referring to FIGS. 15A and 15B, when either of the ramped protrusions 34-8, 34-9 is radially displaced in direction D3 toward central axis 14, cantilever arm 34-7 is also displaced, in a bending motion, in direction D3 toward central axis 14 such that a portion of cantilever arm 34-7, e.g., an upper portion of ramped protrusion 34-8 or 34-9, depresses strike piece 52 in direction D3 toward central axis 14, which in turn releases locking tangs 44-1 from lock opening 36-12 in separator wall 36-9 (see FIG. 5) as described above, thus permitting the pre-compressed cutting cannula spring 38 to decompress to fire cutting cannula slider 44, and in turn cutting cannula 16, in distal direction D2.

In order to effect the displacement of cantilever arm 34-7 of sleeve 34 in direction D3, trigger device 22 includes a proximally extending cantilever arm 22-7 formed as a part of connector bar 22-3. As best shown in the enlarged views of FIGS. 15B and 16, cantilever arm 22-7 has a free end 22-8 that includes a pair of cam follower members 22-9, each having a front cam follower surface 22-10 and a rear cam follower surface 22-11.

Figure 16:
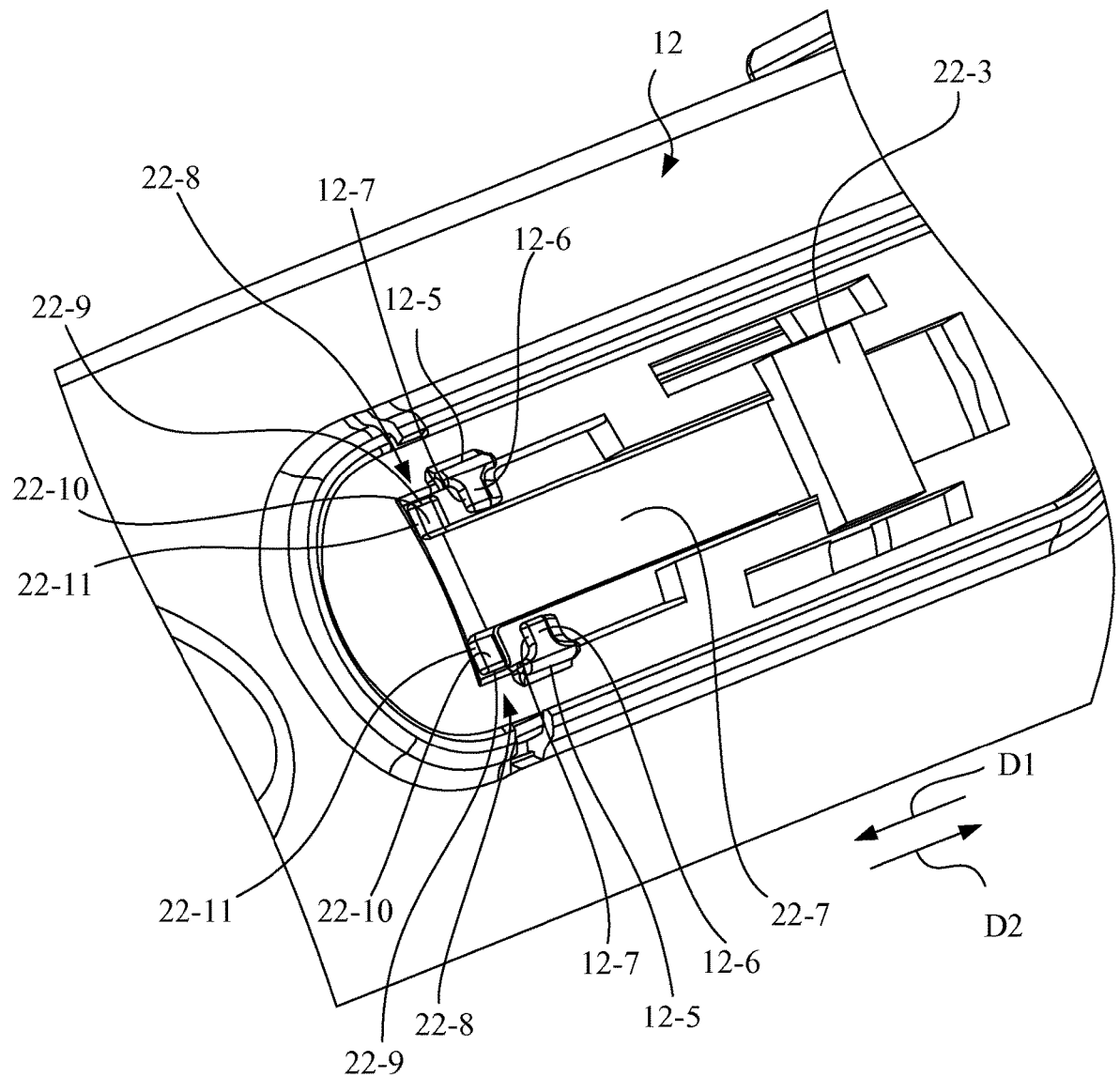
FIG. 16 is an enlarged portion of the core needle biopsy device of FIG. 2 with the side trigger removed to expose a portion of the semi-automatic trigger mechanism of FIG. 15B including the cam and cam follower arrangement.

Referring to FIGS. 15B and 16, outer housing 12 includes a pair of cam rails 12-5 formed as a pair of opposed rails that are angled inwardly toward central axis 14 in the distal direction D2. In the present embodiment, cam rails 12-5 are orientated at an angle in a range of about 40 degrees to 50 degrees with respect to the orientation of central axis 14. Each of cam rails 12-5 includes a front cam surface 12-6 and a rear cam surface 12-7.

When trigger device 22 is moved in distal direction D2, front cam follower surface 22-10 of cam follower members 22-9 of cantilever arm 22-7 will engage rear cam surface 12-7 of cam rails 12-5, and in turn free end 22-8 of cantilever arm 22-7 is displaced in direction D3 toward central axis 14. In the embodiment shown, the free end 22-8 of cantilever arm 22-7 thus engages ramped protrusion 34-9, which in turn is radially displaced in direction D3 toward central axis 14, thereby the free end 34-10 of cantilever arm 34-7 is also displaced, in a bending motion, in direction D3 toward central axis 14 to displace, e.g., depress, strike piece 52 in direction D3 toward central axis 14, which in turn releases locking tangs 44-1 from lock opening 36-12 in separator wall 36-9, thus firing the cutting cannula slider 44, and in turn cutting cannula 16, in distal direction D2.

As front cam follower surface 22-10 of cam follower members 22-9 of cantilever arm 22-7 clears the distal extent of rear cam surface 12-7 of cam rails 12-5, cantilever arm 22-7 will spring back to is steady state position, thus positioning rear cam follower surface 22-11 of cam follower members 22-9 of cantilever arm 22-7 in longitudinal alignment with front cam surface 12-6 of cam rails 12-5. Also, at this time cantilever arm 34-7 will spring back to its steady state position, and spring 54 will return strike piece 52 to its steady state position.

Figure 17:
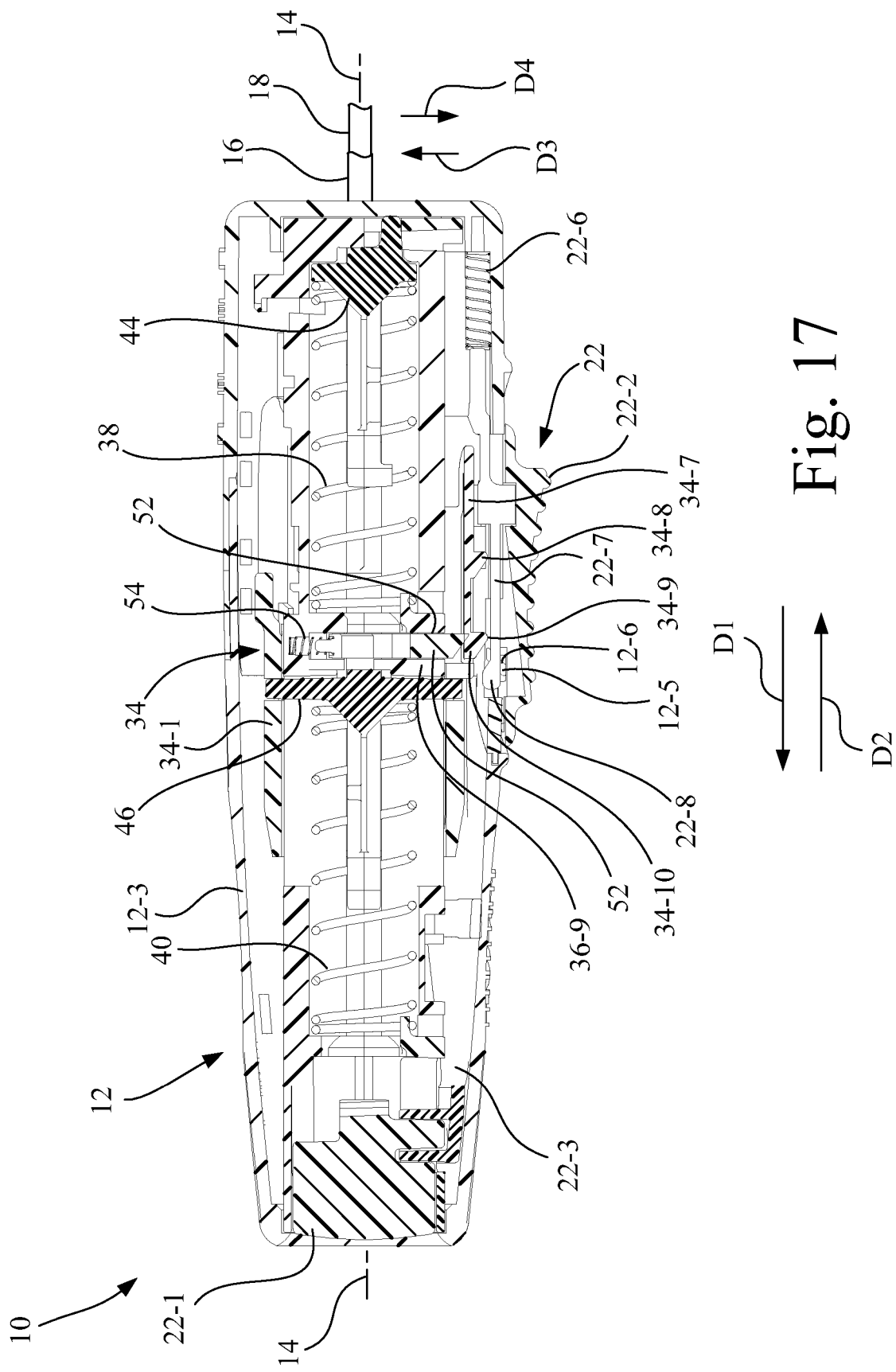
FIG. 17 is a section view of the core needle biopsy device of FIG. 2 taken along plane 14-14, showing the core needle biopsy device in the fully fired, or pre-cocked, state.

When trigger device 22 is released, coil return spring 22-6 moves trigger device in proximal direction D1 toward its home position. During the travel of trigger device 22 in proximal direction D1 to its home position, rear cam follower surface 22-11 of cam follower members 22-9 of cantilever arm 22-7 engages front cam surface 12-6 of cam rails 12-5, which in turn guides the cam follower members 22-9 proximally up the front cam surface 12-6 of cam rails 12-5, thereby displacing free end 22-8 of cantilever arm 22-7 in direction D4 away from central axis 14 until rear cam follower surface 22-11 of cam follower members 22-9 of cantilever arm 22-7 clears the proximal extent of front cam surface 12-6 of cam rails 12-5, at which time cantilever arm 22-7 will spring back to is steady state position, with trigger device 22 now reaching its home position, as illustrated in FIG. 17.

Figure 18:
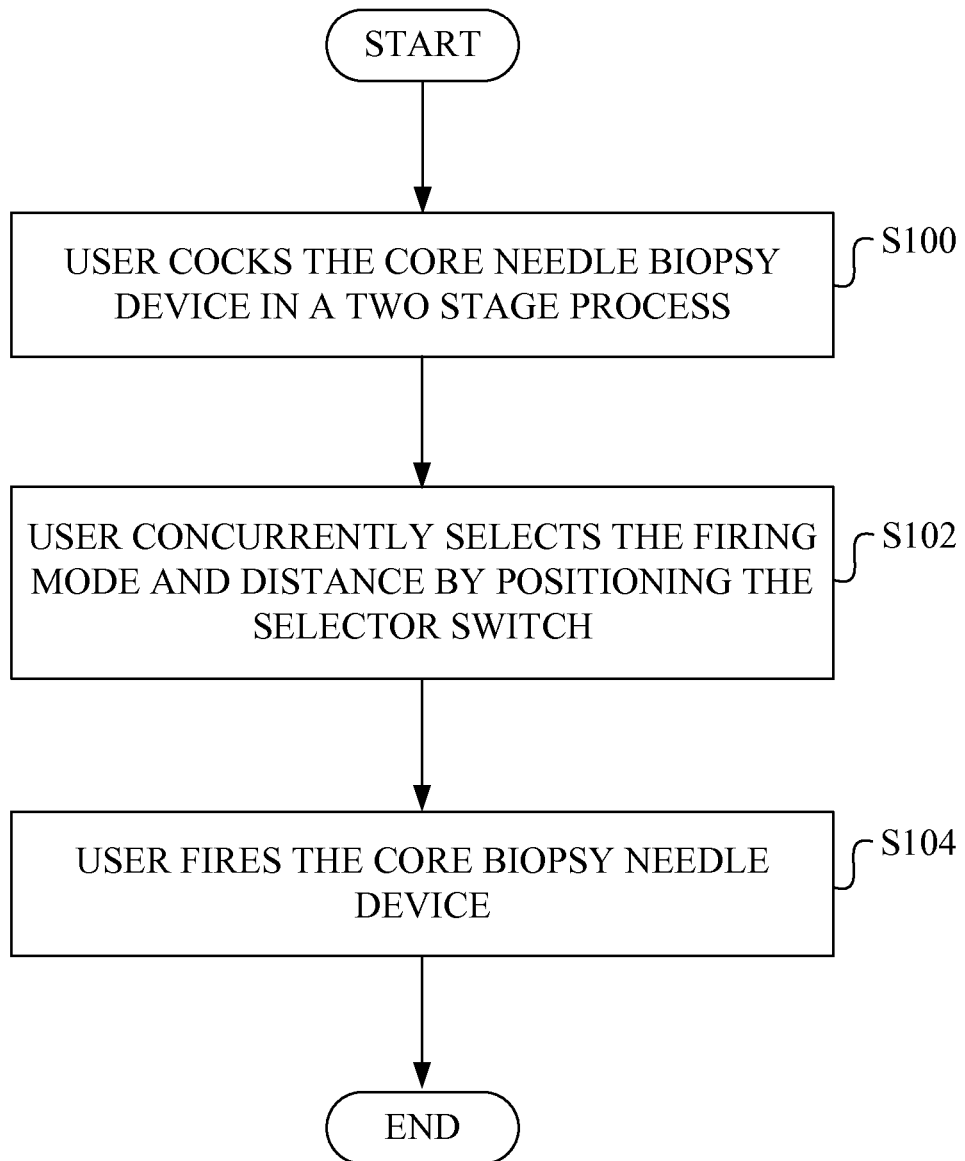
FIG. 18 is a flowchart of the general operation of the core needle biopsy device of the present disclosure, as depicted in FIGS. 1-17.

A general description of the overall operation of core needle biopsy device 10 now follows with further reference to FIG. 18.

At step S100, the user cocks the core needle biopsy device 10 in a two stage process by pulling cocking slider 24 proximally in proximal direction D1. The first retraction of cocking slider 24 locks cutting cannula slider 44 in place through a linear movement of pawl 48 in proximal direction D1 and compresses cutting cannula spring 38. Cocking slider 24 is returned to its starting position via return spring 42. Pawl 48 is then biased by the third leaf spring, opposite to leaf springs 48-4, to contact inner stylet slider 46. The user then retracts the cocking slider 24 a second time in proximal direction D1 to lock inner stylet slider 46 in place and compressed inner stylet spring 40. Core needle biopsy device 10 is now cocked and ready for use (see FIGS. 13 and 14).

At step S102, referring to FIGS. 6 and 9A-9D, the user concurrently selects the firing mode and distance by positioning the selector switch 28. Moving selector switch 28 causes the selector cam 32 to position sleeve 34 to select the desired firing mode, e.g., automatic or semi-automatic, and the desired firing distance, e.g., in the present embodiment 11 mm or 22 mm.

At step S104, the user fires core biopsy needle device 10 by actuating either rear trigger 22-1 or side trigger 22-2 of trigger device 22, thereby moving trigger device 22 in distal direction D2.

When the trigger device 22 is actuated in the automatic mode, inner stylet slider 46 and the attached inner stylet 18 travel forward at a rapid velocity (fire) in distal direction D2 by the decompression of inner stylet spring 40. Simultaneously, sleeve 34, following the track 36-3 (T1 for 11 mm, or T3 for 22 mm; see FIG. 8) in sub-frame 36, travels forward depressing the ramped protrusion 52-1 on strike piece 52 which subsequently squeezes the locking tangs 44-1 on cutting cannula slider 44 causing cutting cannula slider 44 and the attached cutting cannula 16 to also travel forward at a rapid velocity (fire) in distal direction D2 by the decompression of cutting cannula spring 38.

When the trigger device 22 is actuated a first time in the semi-automatic mode, inner stylet slider 46 and the attached inner stylet 18 travel forward at a rapid velocity (fire) in distal direction D2 by the decompression of inner stylet spring 40. Simultaneously, sleeve 34 following track 36-3 (T2 for both 11 mm and 22 mm; see FIG. 8) in sub-frame 36, travels longitudinally but is rotationally positioned such that sleeve 34 does not depress strike piece 52. When trigger device 22 is actuated a second time, the ramped protrusion 52-1 on strike piece 52 is depressed, which in turn squeezes, e.g., radially displaces, the locking tangs 44-1 on cutting cannula slider 44 in a direction perpendicular to central axis 14 to cause cutting cannula slider 44 and the attached cutting cannula 16 to also travel forward at a rapid velocity (fire) in distal direction D2 by the decompression of cutting cannula spring 38.

While this present disclosure has been described with respect to at least one embodiment, the present disclosure can be further modified within the spirit and scope of this disclosure. This application is therefore intended to cover any variations, uses, or adaptations of the present disclosure using its general principles. Further, this application is intended to cover such departures from the present disclosure as come within known or customary practice in the art to which this disclosure pertains and which fall within the limits of the appended claims.

What is claimed is:

1. A method of operating a biopsy device, the method comprising:
    operating a cocking mechanism of the biopsy device, wherein the cocking mechanism retracts each of a cutting cannula of a cutting cannula mechanism and an inner stylet of an inner stylet mechanism, wherein the inner stylet is coaxial with the cutting cannula;
    selecting with a selector assembly a desired operation mode-distance combination from a plurality of user selectable operating modes and a plurality of user selectable firing distances, the selector assembly comprising a single selector switch having an exterior tab accessible by a user, the plurality of user selectable operating modes having at least two user selectable operating modes and the plurality of user selectable firing distances having at least two user selectable firing distances, wherein a firing distance is a distance of distal travel of each of the inner stylet and the cutting cannula in a distal direction opposite a proximal direction from a cocked position;

actuating a trigger device of the biopsy device to fire at least one of the inner stylet mechanism and the cutting cannula mechanism to advance the respective at least one of the inner stylet and the cutting cannula from the cocked position in the distal direction.

2. The method of claim 1, wherein the single selector switch has a plurality of selector switch positions, wherein the plurality of selector switch positions include a plurality of mode-distance combinations including: an automatic mode and a first firing distance, a semi-automatic mode and the first firing distance, the automatic mode and a second firing distance, and the semi-automatic mode and the second firing distance, and wherein in the automatic mode the inner stylet and the cutting cannula are sequentially fired from the cocked position by a single actuation of the trigger device, and in the semi-automatic mode the inner stylet is fired from the cocked position by a first actuation of the trigger device and the cutting cannula is fired from the cocked position by a second actuation of the trigger device.

3. The method of claim 2, wherein the single selector switch has a first cam track and a second cam track, each of the first cam track and the second cam track being formed as a single continuous track having at least three adjoining track segments having end points that correspond to the plurality of mode-distance combinations of the plurality of selector switch positions.

4. The method of claim 1, wherein the single selector switch has a first cam track and a second cam track, each of the first cam track and the second cam track being formed as a single continuous track having at least three adjoining track segments having end points that correspond to a plurality of mode-distance combinations.

5. The method of claim 1, wherein:
the biopsy device comprises a sub-frame comprising a separator wall and a proximal end wall, the sub-frame configured to define a distal interior chamber and a proximal interior chamber which are divided by the separator wall, the separator wall having a first lock opening and the proximal end wall having a second lock opening, the sub-frame having a first rack gear;
the cutting cannula mechanism has a cutting cannula slider and a cutting cannula spring, the cutting cannula slider being fixed to a proximal end of the cutting cannula, the cutting cannula slider having a first locking tang configured to selectively engage the first lock opening of the separator wall, the cutting cannula spring being interposed between the cutting cannula slider and the separator wall;
the inner stylet mechanism has an inner stylet slider fixed to a proximal end of the inner stylet, the inner stylet slider having a second locking tang configured to selectively engage the second lock opening of the proximal end wall, and an inner stylet spring being interposed between the inner stylet slider and an end wall of the sub-frame; and
the cocking mechanism includes a cocking slider, a pawl, and a rotary gear, the cocking slider having a second rack gear, the rotary gear being interposed between the first rack gear of the sub-frame and the second rack gear of the cocking slider, the pawl having a proximal end, a distal end and a mid-portion between the proximal end and the distal end, the mid-portion of the pawl being configured to rotatably mount the rotary gear, the pawl configured to interact with each of the cutting cannula slider and the inner stylet slider.

6. The method of claim 5, wherein the biopsy device is configured such that a first movement of the cocking slider in the proximal direction causes a first rotation of the rotary gear, and in turn causes a first linear displacement of the pawl in the proximal direction, the distal end of the pawl having a hook member configured to engage the cutting cannula slider to pull the cutting cannula slider in the proximal direction and compress the cutting cannula spring, the first locking tang of the cutting cannula slider configured to pass through the first lock opening of the separator wall to retain the cutting cannula slider and the cutting cannula in the cocked position.

7. The method of claim 6, wherein the biopsy device further comprises a return spring configured to move the cocking slider in the distal direction to return the cocking slider and the pawl to a home position.

8. The method of claim 7, wherein the biopsy device is configured such that a second movement of the cocking slider in the proximal direction causes a second rotation of the rotary gear, and in turn causes a second linear displacement of the pawl in the proximal direction, the proximal end of the pawl configured to engage the inner stylet slider to push the inner stylet slider in the proximal direction and compress the inner stylet spring, the second locking tang of the inner stylet slider configured to pass through the second lock opening of the proximal end wall to retain the inner stylet slider and the inner stylet in the cocked position.

9. The method of claim 5, further comprising selectively operating the biopsy device in an automatic mode and a semi-automatic mode depending on a position of the single selector switch, the biopsy device further comprising:
a sleeve configured as a cylindrical body that is rotatable and longitudinally movable with respect to the sub-frame; and
a strike piece configured to release the first locking tang of the cutting cannula slider when moved in a direction perpendicular to a cannula axis,
wherein in the automatic mode, the biopsy device is configured such that an actuation of the trigger device releases the second locking tang of the inner stylet slider from the proximal end wall to fire the inner stylet slider and the inner stylet in the distal direction by a decompression of the inner stylet spring, and the sleeve is coupled with the inner stylet slider to move in the distal direction along the cannula axis, and the sleeve is configured to depress the strike piece in the direction perpendicular to the cannula axis to release the first locking tang of the cutting cannula slider from the separator wall to fire the cutting cannula slider and the cutting cannula in the distal direction by a decompression of the cutting cannula spring, and
wherein in the semi-automatic mode, the biopsy device is configured such that a first actuation of the trigger device releases the second locking tang of the inner stylet slider from the proximal end wall to fire the inner stylet slider and the inner stylet in the distal direction by the decompression of the inner stylet spring, and a second actuation of the trigger device depresses the strike piece in the direction perpendicular to the cannula axis to release the first locking tang of the cutting cannula slider from the separator wall to fire the cutting cannula slider and the cutting cannula in the distal direction by the decompression of the cutting cannula spring.

10. A method of operating a biopsy device, the method comprising:
providing a housing defining an interior chamber having a central axis;
providing a sub-frame positioned in the interior chamber of the housing, the sub-frame having a separator wall and a proximal end wall, the sub-frame configured to define a distal interior chamber and a proximal interior chamber which are divided by the separator wall, the separator wall having a first lock opening and the proximal end wall having a second lock opening, the sub-frame having a first rack gear;
providing a cutting cannula mechanism having a cutting cannula, a cutting cannula slider, and a cutting cannula spring, the cutting cannula slider being fixed to a proximal end of the cutting cannula, the cutting cannula slider having a first locking tang;
selectively engaging the first lock opening of the separator wall, the cutting cannula spring being interposed between the cutting cannula slider and the separator wall;
providing a stylet mechanism comprising an inner stylet, the inner stylet having an inner stylet slider fixed to a proximal end of the inner stylet, the inner stylet slider having a second locking tang;
selectively engaging the second lock opening of the proximal end wall, an inner stylet spring being interposed between the inner stylet slider and the proximal end wall; and
providing a cocking mechanism including a cocking slider, a pawl, and a rotary gear, the cocking slider having a second rack gear, the rotary gear being interposed between the first rack gear of the sub-frame and the second rack gear of the cocking slider, the pawl having a proximal end, a distal end and a mid-portion between the proximal end and the distal end, the mid-portion of the pawl being configured to rotatably mount the rotary gear, the pawl configured to interact with each of the cutting cannula slider and the inner stylet slider.

11. The method of claim 10, further comprising:
moving the cocking slider a first movement in a proximal direction thereby causing a first rotation of the rotary gear, which in turn causes a first linear displacement of the pawl in the proximal direction; and
engaging a hook member at the distal end of the pawl with the cutting cannula slider to pull the cutting cannula slider in the proximal direction and compress the cutting cannula spring,
passing the first locking tang of the cutting cannula slider through the first lock opening of the separator wall to retain the cutting cannula slider and the cutting cannula in a cocked position.

12. The method of claim 11, further comprising moving the cocking slider in a distal direction opposite the proximal direction with a return spring to return the cocking slider and the pawl to a home position.

13. The method of claim 12, further comprising moving the cocking slider a second movement in the proximal direction thereby causing a second rotation of the rotary gear, and in turn causing a second linear displacement of the pawl in the proximal direction;
engaging the inner stylet slider with the proximal end of the pawl to push the inner stylet slider in the proximal direction and compress the inner stylet spring; and
passing the second locking tang of the inner stylet slider through the second lock opening of the proximal end wall to retain the inner stylet slider and the inner stylet in the cocked position.

14. The method of claim 13, further comprising:
providing a trigger device; and sequentially:
releasing the second locking tang of the inner stylet slider from the proximal end wall to fire the inner stylet slider and the inner stylet in the distal direction by a decompression of the inner stylet spring, and
releasing the first locking tang of the cutting cannula slider from the separator wall to fire the cutting cannula slider and the cutting cannula in the distal direction by decompression of the cutting cannula spring.

15. The method of claim 12, further comprising:
providing a trigger device;
providing a sleeve configured as a cylindrical body that is rotatable and longitudinally movable with respect to the sub-frame;
providing a strike piece configured to release the first locking tang of the cutting cannula slider when moved in a direction perpendicular to the central axis; and
in an automatic mode, actuating the trigger device to release the second locking tang of the inner stylet slider from the proximal end wall to fire the inner stylet slider and the inner stylet in the distal direction by a decompression of the inner stylet spring, the sleeve being coupled with the inner stylet slider to move in the distal direction along the central axis, and the sleeve is configured to depress the strike piece in the direction perpendicular to the central axis to release the first locking tang of the cutting cannula slider to fire the cutting cannula slider and the cutting cannula in the distal direction by a decompression of the cutting cannula spring; or
in a semi-automatic mode, actuating the trigger device a first actuation that releases the second locking tang of the inner stylet slider from the proximal end wall to fire the inner stylet slider and the inner stylet in the distal direction by the decompression of the inner stylet spring; and
actuating the trigger device a second actuation that depresses the strike piece in the direction perpendicular to the central axis to release the first locking tang of the cutting cannula slider to fire the cutting cannula slider and the cutting cannula in the distal direction by the decompression of the cutting cannula spring.

16. The method of claim 10, further comprising
selectively positioning a selector assembly in one of four selector switch positions with an exterior tab, the selector assembly configured to concurrently select between two user selectable operating modes and to select between two user selectable firing distances, wherein a firing distance is a distance of distal travel of each of the inner stylet and the cutting cannula in a distal direction from a cocked position.

17. The method of claim 16, wherein the biopsy device further comprises a trigger device,
wherein the four selector switch positions are four mode-distance combinations consisting of: an automatic mode and a first firing distance, a semi-automatic mode and the first distance, the automatic mode and a second firing distance, and the semi-automatic mode and the second firing distance, and wherein in the automatic mode the inner stylet and the cutting cannula are sequentially fired from the cocked position by a single actuation of the trigger device, and in the semi-automatic mode the inner stylet is fired from the cocked position by a first actuation of the trigger device and the cutting cannula is fired from the cocked position by a second actuation of the trigger device.

18. The method of claim 17, further comprising
positioning each of the inner stylet and the cutting cannula in the cocked position with the cocking mechanism, wherein each of the inner stylet spring and the cutting cannula spring is compressed to ready the biopsy device for a firing operation;

providing a selector switch having a first cam track and a second cam track, each of the first cam track and the second cam track being formed as a single continuous track having three adjoining track segments that correspond to the four mode-distance combinations, wherein the sub-frame is configured to define a sub-frame track having three track portions;

providing a sleeve configured as a cylindrical body that is rotatable and longitudinally movable with respect to the sub-frame;

providing a selector stop that includes a body having a proximal end that has an upwardly extending pin;

engaging the selector stop in the first cam track of the selector switch, the selector stop configured to impede a linear motion of the sleeve along the central axis in the distal direction with respect to the firing distance selected by the selector switch;

providing a selector cam that includes a lateral body having a shallow V-shaped cam surface with a side notch at an apex of the cam surface, and having an upwardly extending pin, the upwardly extending pin;

engaging the selector cam in the second cam track of the selector switch, wherein the sleeve has a cantilever arm having a first sleeve pin;

engaging the first sleeve pin configured to the cam surface;

guiding the first sleeve pin into the side notch of the selector cam, wherein a rotational position of the sleeve is determined based on a selected switch position of the four selector switch positions of the selector switch; and engaging a second sleeve pin extending from an inner surface of the sleeve and following one of the three track portions of the sub-frame during movement of the sleeve in the distal direction, wherein a selected track portion is determined by the rotational position of the sleeve as determined by the selected switch position of the four selector switch positions of the selector switch.

19. The method of claim 18, wherein the selected track portion of the sub-frame that is followed by the second sleeve pin of the sleeve at least in part determines the different modes and the different firing distances of the inner stylet and the cutting cannula.

20. The method of claim 19, further comprising:
releasing the first locking tang of the cutting cannula slider with a strike piece by moving the strike piece in a direction perpendicular to the central axis, wherein in the automatic mode the biopsy device configured such that an actuation of the trigger device releases the second locking tang of the inner stylet slider from the proximal end wall to fire the inner stylet slider and the inner stylet in the distal direction by a decompression of the inner stylet spring, and the sleeve is coupled with the inner stylet slider to move in the distal direction along the central axis, and the sleeve is configured to depress the strike piece in the direction perpendicular to the central axis to release the first locking tang of the cutting cannula slider to fire the cutting cannula slider and the cutting cannula in the distal direction by a decompression of the cutting cannula spring, and wherein in the semi-automatic mode, the biopsy device configured such that the first actuation of the trigger device releases the second locking tang of the inner stylet slider from the proximal end wall to fire the inner stylet slider and the inner stylet in the distal direction by the decompression of the inner stylet spring, and the second actuation of the trigger device depresses the strike piece in the direction perpendicular to the central axis to release the first locking tang of the cutting cannula slider to fire the cutting cannula slider and the cutting cannula in the distal direction by the decompression of the cutting cannula spring.

* * * * *